United States Patent [19]
Hallahan et al.

[11] Patent Number: 5,962,424
[45] Date of Patent: Oct. 5, 1999

[54] METHODS AND COMPOSITIONS FOR TARGETING SELECTINS

[75] Inventors: Dennis E. Hallahan, Park Ridge; Ralph R. Weichselbaum, Chicago, both of Ill.

[73] Assignee: Arch Development Corporation, Chicago, Ill.

[21] Appl. No.: 08/392,541

[22] Filed: Feb. 21, 1995

[51] Int. Cl.$^6$ ........................................... A01N 43/04
[52] U.S. Cl. ...................... 514/44; 424/93.21; 424/320.1; 424/69.1; 424/455; 424/458; 536/24.1
[58] Field of Search ........................... 514/44; 424/93.21; 435/320.1, 172.3, 69.1, 455, 458; 536/24.1; 935/6, 34, 59, 62

[56] References Cited

FOREIGN PATENT DOCUMENTS

| 92/11033 | 7/1992 | WIPO . |
| WO 92/19646 | 11/1992 | WIPO . |
| WO 94/00477 | 1/1994 | WIPO . |
| WO 94/29342 | 12/1994 | WIPO . |
| WO 95/26403 | 10/1995 | WIPO . |

OTHER PUBLICATIONS

Mastrangelo et al., J Seminars in Oncology, vol. 23, 1:4–21, 1996.
Ledley, Human Gene Therapy, 6:1129–1144, 1995.
Gunzburg et al., Molecular Medicine Today, 1995, 410–417, 1995.
Weichselbaum et al, Int. J. Radiation Oncology, 24:565–567 (1992).
Cameron et al., J. Exp. Medicine, 171:249–263 (1990).
Salmi et al., J. Immunology, 154:6002–6012 (1995).
Abbassi et al., "E–Selectin Supports Neutrophil Rolling In Vitro Under Conditions of Flow," *J. Clin. Invest.*, 92:2719–2730, Dec. 1993.
Bicknell, "Vascular Targeting and the Inhibition of Angiogenesis," *Annals. of Oncology*, 5(Suppl. 4):S45–S50, 1994.
Cavenagh et al., "Acute Myeloid Leukaemia Blast Cells Bind to Human Endothelium In Vitro Utilizing E–Selectin and Vascular Cell Adhesion Molecule–1 (VCAM–1)," *British Journal of Haematology*, 85:285–291, 1993.
Chapman et al., "Noninvasive Imaging of E–Selectin Expression by Activated Endothelium in Urate Crystal–Induced Arthritis," *Arthritis & Rheumatism*, 37(12):1752–1756, Dec. 1994.
Collins, "Biology of Disease, Endothelial Nuclear Factor–κB and The Initiation of the Atherosclerotic Lesion," *Laboratory Investigation*, 68(5):499, 1993.
De Boer et al., "Functional Evidence that the HECA–452 Antigen is Involved in the Adhesion of Human Neutrophils and Lymphocytes to Tumour Necrosis Factor–α–Stimulated Endothelial Cells," *Immunology*, 81:359–365, 1994.
Finco and Baldwin, "κB Site–Dependent Induction of Gene Expression by Diverse Inducers of Nuclear Factor κB Requires Raf–1," *The Journal of Biological Chemistry*, 268(24):17676–17679, Aug. 1993.

Ghersa et al., "Labile Proteins Play a Dual Role in the Control of Endothelial Leukocyte Adhesion Molecule–1 (ELAM–1) Gene Regulation," *The Journal of Biological Chemistry*, 267(27):19226–19232, Sep. 1992.
Goelz et al., "Differential Expression of an E–Selectin Ligand (SLe$^x$) by Two Chinese Hamster Ovary Cell Lines Transfected with the Same α(1,3)–Fucosyltransferase Gene (ELFT)," *The Journal of Biological Chemistry*, 269(2):1033–1040, Jan. 1994.
Gosset et al., "Expression of E–Selectin, ICAM–1 and VCAM–1 on Bronchial Biopsies from Allergic and Non–Allergic Asthmatic Patients," *Int. Arch. Allergy Immunol.*, 106:69–77, 1995.
Green et al., "High Affinity Binding of the Leucocyte Adhesion Molecule L–Selectin to 3'–Sulphated–Le$^a$ and –Le$^x$ Oligosaccharides and the Predominance of Sulphate in this Interaction Demonstrated by Binding Studies with a Series of Lipid–Linked Oligosaccharides," *Biochemical and Biophysical Research Communications*, 188(1):244–251, Oct. 1992.
Grinnell et al., "Human Protein C inhibits selectin–mediated cell adhesion: role of unique fucosylated oligosaccharide," *Glycobiology*, 4(2):221–225, 1994.
Groves et al., "Endothelial Leucocyte Adhesion Molecule–1 (ELAM–1) Expression in Cutaneous Inflammation," *British Journal of Dermatology*, 124:117–123, 1991.
Hallahan et al., "Increased Tumor Necrosis Factor α mRNA After Cellular Exposure to Ionizing Radiation," *Proc. Natl. Acad. Sci. USA*, 86:10104–10107, Dec. 1989.
Hallahan et al., "Transcriptional Regulation of the TNF Gene by x–Irradiation," *Proc. Am. Assoc. Cancer Res.*, 31(0):75, Mar. 1990.
Hallahan et al., "Tumor Necrosis Factor Gene Expression is Mediated by Protein Kinase C Following Activation by Ionizing Radiation," *Cancer Research*, 51:4565–4569, Sep. 1991.
Hallahan et al., "Radiation Signaling Mediated by Jun Activation Following Dissociation from a Cell Type–Specific Repressor," *The Journal of Biological Chemistry*, 268(7):4903–4907, Mar. 1993.
Hallahan et al., "The Role of Cytokines in Radiation Oncology," *Important Advances in Oncology*, 1993.
Hallahan et al., "Membrane–Derived Second Messenger Regulates X–Ray–Mediated Tumor Necrosis Factor α Gene Induction," *Proc. Natl. Acad. Sci. USA*, 91:4897–4901, May 1994.

(List continued on next page.)

*Primary Examiner*—Bruce R. Campbell
*Assistant Examiner*—Dave Trong Nguyen
*Attorney, Agent, or Firm*—Arnold, White & Durkee

[57] ABSTRACT

Disclosed are a variety of compositions and methods for use in specifically targeting the L-selectin or preferably, the E-selectin marker following its cell surface induction, e.g., using ionizing radiation, in tumor vasculature endothelial cells. The compositions and methods described are suitable for use in the delivery of selected agents to tumor vasculature, as may be used in the diagnosis aid therapy of solid tumors.

25 Claims, 8 Drawing Sheets

OTHER PUBLICATIONS

Harris et al., "Gene Therapy Through Signal Transduction Pathways and Angiogenic Growth Factors as Therapeutic Targets in Breast Cancer," *Cancer Supplement*, 74(3):1021–1025, Aug. 1994.

Hasegawa et al., "Synthesis of Deoxy–L–Fucose–Containing Sialyl Lewis X Ganglioside Analogues," *Carbohydrate Research*, 257:67–80, 1994.

Hwu et al., "Functional and Molecular Characterization of Tumor–Infiltrating Lymphocytes Transduced with Tumor Necrosis Factor–α cDNA for the Gene Therapy of Cancer in Humans," *The Journal of Immunology*, 150(9):4104–4115, May 1993.

Jutila et al., "Characterization of a Functionally Important and Evolutionarily Well–Conserved Epitope Mapped to the Short Consensus Repeats of E–Selectin and L–Selectin," *J. Exp. Med.*, 175:1565–1573, Jun. 1992.

Keelan et al., "Characterization of E–Selectin Expression In Vivo with Use of a Radiolabeled Monoclonal Antibody," *Am. J. Physiol.*, 266(1 Pt 2):H279–H290, Jan. 1994.

Keelan et al., "Imaging Vascular Endothelial Activation: An Approach Using Radiolabeled Monoclonal Antibodies Against the Endothelial Cell Adhesion Molecule E–Selectin," *The Journal of Nuclear Medicine*, 35(2):276–281, Feb. 1994.

Kojima et al., "Multi–Recognition Capability of E–Selectin in a Dynamic Flow System, as Evidenced by Differential Effects of Sialidases and Anti–Carbohydrate Antibodies on Selectin–Mediated Cell Adhesion at Low vs. High Wall Shear Stress: A Preliminary Note," *Biochemical and Biophysical Research Communications*, 189(3):1686–1694, Dec. 1992.

Lo et al., "E–Selectin Ligands Mediate Tumor Necrosis Factor–Induced Neutrophil Sequestration and Pulmonary Edema in Guinea Pig Lungs," *Circulation Research*, 75(6):955–960, Dec. 1994.

Montefort et al., "Intercellular Adhesion Molecule–1 (ICAM–1) and Endothelial Leucocyte Adhesion Molecule–1 (ELAM–1) Expression int he Bronchial Mucosa of Normal and Asthmatic Subjects," *Eur. Respir. J.*, 5:815–823, 1992.

Montgomery et al., "Activation of Endothelial–Leukocyte Adhesion Molecule 1 (ELAM–1) Gene Transcription," *Proc. natl. Acad. Sci. USA*, 88:6523–6527, Aug. 1991.

Moughal et al., Endothelial Cell Leukocyte Adhesion Molecule–1 (ELMA–1) and Intercellular Adhesion Molecule–1 (ICAM–1) Expression in Gingival Tissue During Health and Experimentally–Induced Gingivitis, *J. Periodont. Res.*, 27:623–630, 1992.

Mulligan et al., "Protective Effects of Sialylated Oligosaccharides in Immune Complex–Induced Acute Lung Injury," *J. Exp. Med.*, 178:623–631, Aug. 1993.

Nabel et al., "Gene Transfer and Vascular Disease," *Cardiovascular Research*, 28:445–455, 1994.

Rao et al., "Sialyl Lewis X Mimics Derived from a Pharmacophore Search are Selectin Inhibitors with Anti–inflammatory Activity," *The Journal of Biological Chemistry*, 269(31):19663–19666, Aug. 1994.

Nelson et al., "Higher–Affinity Oligosaccharide Ligands for E–Selectin," *J. Clin. Invest.*, 91:1157–1166, Mar. 1993.

Neumann et al., "Immunohistochemistry of Port–Wine Stains and Normal Skin with Endothelium–Specific Antibodies PAL–E, Anti–ICAM–1, Anti–ELAM–1, and Anti–Factor VIIIrAg," *Arch Dermatol.*, 130:879–883, Jul. 1994.

Norton et al., "Characterization of Murine E–Selectin Expression In Vitro Using Novel Anti–Mouse E–Selectin Monoclonal Antibodies," *Biochemical and Biophysical Research Communications*, 195(1):250–258, Aug. 1993.

Ohno et al., "Gene Therapy for Vascular Smooth Muscle Cell Proliferation After Arterial Injury," *Science*, 265:781–784, Aug. 1994.

Olofsson et al., "E–Selectin Mediates Leukocyte Rolling in Interleukin–1–Treated Rabbit Mesentery Venules," *Blood*, 84(8):2749–2758, Oct. 1994.

Pai et al., "Antitumor Effects of B3–PE and B3–LysPE40 in a Nude Mouse Model of Human Breast Cancer and the Evaluation of B3–PE Toxicity in Monkeys," *Cancer Research*, 52:3189–3193, Jun. 1992.

Phillips et al., "ELAM–1 Mediates Cell Adhesion by Recognition of a Carbohydrate Ligand, Sialyl–Le$^x$," *Science*, 250:1130–1132, Nov. 1990.

Sedmak et al., "Divergent Patterns of ELAM–1, ICAM–1, and VCAM–1 Expression on Cytomegalovirus–Infected Endothelial Cells," *Transplantation*, 58(12):1379–1385, Dec. 1994.

Sherman et al., "Ionizing Radiation Regulates Expression of the C–Jun Prot–Oncogene," *Proc. Am. Assoc. Cancer Res.*, 31(0):13, Mar. 1990.

Silber et al., "Recruitment of Lymphocytes During Cutaneous Delayed Hypersensitivity in Nonhuman Primates is Dependent on E–Selectin and Vascular Cell Adhesion Molecule 1," *J. Clin. Invest.*, 93(1554–1563, Apr. 1994.

Span et al., "Cytomegalovirus Induced PMN Adherence in Relation to an ELAM–1 Antigen Present on Infected Endothelial Cell Monolayers," *Immunology*, 72:355–360, 1991.

Sporn et al., "E–Selectin–Dependent Neutrophil Adhesion to *Rickettsia Rickettsii*–Infected Endothelial Cells," *Blood*, 81(9):2406–2412, May 1993.

Springer, "Traffic Signals for Lymphocyte Recirculation and Leukocyte Emigration: The Multistep Paradigm," *Cell*, 76:301–314, Jan. 1994.

Steinberg et al., "Survival in Lung Reperfusion Injury is Improved by an Antibody that Binds and Inhibits L– and E–Selectin," *The Journal of Heart and Lung Transplantation*, 13(2):306–318, Mar./Apr. 1994.

Swerlick and Lawley, "Role of Microvascular Endothelial Cells in Inflammation," *The Journal of Investigative Dermatology*, 100(1):111S–115S, Jan. 1993.

Tyrrell et al., "Structural Requirements for the Carbohydrate Ligand of E–Selectin," *Proc. Natl. Acad. Sci. USA*, 88:10372–10376, Nov. 1991.

Uckun et al., "Ionizing Radiation Stimulates Unidentified Tyrosine–Specific Protein Kinases in Human B–Lymphocyte Precursors, Triggering Apoptosis and Clonogenic Cell Death," *Proc. Natl. Acad. Sci. USA*, 89:9005–9009, Oct. 1992.

Ulich et al., "Intratracheal Administration of Endotoxin and Cytokines: VIII. LPS Induces E–Selectin Expression; Anti–E–Selectin and Soluble E–Selectin Inhibit Acute Inflammation," *Inflammation*, 18(4):389–398, 1994.

Veale et al., "Reduced Synovial Membrane Macrophage Numbers, ELAM–1 Expression, and Lining Layer Hyperplasia in Psoriatic Arthritis as Compared with Rheumatoid Arthritis," *Arthritis and Rheumatism*, 36(7):893–900, Jul. 1993.

von Asmuth et al., "Evidence for Endocytosis of E–Selectin in Human Endothelial Cells," *Eur. J. Immunol.*, 22:2519–2526, 1992.

Wakita et al., "E–Selectin and Vascular Cell Adhesion Molecule–1 as Critical Adhesion Molecules for Infiltration of T Lymphocytes and Eosinophils in Atopic Dermatitis," *J. Cutan. Pathol.*, 33–39, 1994.

Walz et al., "Recognition by ELAM–1 of the Sialyl–Le$^x$ Determinant on Myeloid and Tumor Cells," *Science*, 250:1132–1135, Nov. 1990.

Weichselbaum et al., "Gene Therapy Targeted by Radiation Preferentially Radiosensitizes Tumor Cells," *Cancer Research*, 54:4266–4269, Aug. 1994.

Whelan et al., "An NF κB–Like Factor is Essential but not Sufficient for Cytokine Induction of Endothelial Leukocyte Adhesion Molecule 1 (ELAM–1) Gene Transcription," *Nucleic Acids Research*, 19(10):2645–2653, 1991.

Yuen et al., "Novel Sulfated Ligands for the Cell Adhesion Molecule E–Selectin Revealed by the Neoglycolipid Technology Among O–Linked Oligosaccharides on an Ovarian Cystadenoma Glycoprotein," *Biochemistry*, 31:9126–9131, 1992.

Yuen et al., "Sulfated Blood Group Lewis," *The Journal of Biological Chemistry*, 269(3):1595–1598, Jan. 1994.

Zhang et al., "A Secreted Mucin Carrying Sialyl–Lewis a From Colon Carcinoma Cells Binds to E–Selectin and Inhibits HL–60 Cell Adhesion," *Int. J. Cancer*, 59:823–829, 1994.

Bonni et al., "Characterization of a Pathway for Ciliary Neurotrophic Factor Signaling to the Nucleus," *Science*, 262:1575–1579, 1993.

Cantley et al., "Oncogenes and Signal Transduction," *Cell*, 64:281–302, 1991.

Carter et al., "Tyrosine phosphorylation of phospholipase C induced by membrane immunoglobulin in B lymphocytes," *Proc. Natl. Acad. Sci. USA*, 88:2745–2749, 1991.

Casillas et al., "Stimulation of B–cells via the Membrane Immunoglobulin Receptor or with Phorbol Myristate 13–Acetate Induces Tyrosine Phosphorylation and Activation of a 42–kDa Microtubule–associated Protein–2 Kinase," *The Journal of Biological Chemistry*, 266(28):19088–19094, 1991.

Chou and Roizman, "The $g_1$34.5 Gene of Herpes Simplex Virus 1 Precludes Neuroblastoma Cells from Triggering Total Shutoff of Protein Synthesis Characteristic of Programmed Cell Death in Neuronal Cells," *Proc. Natl. Acad. Sci. USA*, 89:3266–3270, 1992.

Christy et al., "A gene activated in mouse 3T3 cells by serum growth factors encodes a protein with 'zinc finger' sequences," *Proc. Natl. Acad. Sci. USA*, 85:7857–7861, 1988.

Gillespie et al., "Inhibition of pancreatic Cancer Cell Growth In Vitro by the Tyrphostin Group of Tyrosine Kinase Inhibitors," *Br. J. Cancer*, 68:1122–1126, 1993.

Gould et al., Complementation of the Mitotic Activator, p80$^{cdc25}$, by a Human Protein–Tyrosine Phosphata *Science*, 250:1573–1576, 1990.

Ohmichi et al., "The Tyrosine Kinase Inhibitor Tyrphostin Blocks the Cellular Actions of Nerve Growth Factor," *Biochemistry*, 32:4650–4658, 1993.

Berg et al., "Antibodies Cross–Reactive with E– and P–Selectin Block Both E– and P–Selectin Functions," *Blood*, 85(1):31–37, Jan. 1995.

Budavari et al., Ed., "The Merck Index, An Encyclopedia of Chemicals, Drugs, and Biologicals," *Merck & Co., Inc.*, Rahway, NJ, pp. 280,562 and 708, 1989.

Colombo et al., "Hypoxic Tumor Cell Death and Modulation of Endothelial Adhesion Molecules in the Regression of Granulocyte Colony–Stimulating Factor–Transduced Tumors," *Am. J. Pathol.*, 148(2):473–483, Feb. 1996.

DeBois et al., "New Agents for Scintigraphy in Rheumatoid Arthritis," *European Journal of Nuclear Medicine*, 22(11):1339–1346, Nov. 1995.

Hallahan et al., "E–Selectin Gene Induction by Ionizing Radiation is Independent of Cytokine Induction," *Biochemical and Biophysical Research*, 217(3):784–795, Dec. 1995.

Hallahan et al, "The E–Selectin Promoter is a Novel Radiation–Induced Gene in Endothelial Cells," *Proceedings of the American Association for Cancer Research Annual Meetings*, 36:605, Abstract No. 3598, Toronto, Ontario, Canada, Mar. 18–22, 1995.

Jamar et al., Inflammatory Arthritis: Imaging of Endothelial Cell Activation with an indium–111–labeled F(ab')2 Fragment of Anti–E–Selectin Monoclonal Antibody, *Radiology*, 194(3):843–850, Mar. 1995.

Kiely et al., "Immunoselective Targeting of an Anti–Thrombin Agent to the Surface of Cytokine–Activated Vascular Endothelial Cells," *Arterioscler, Thromb., Vasc. Biol.*, 15(8):1211–1218, Aug. 1995.

Leirisalo–Repo, "The Present Knowledge of the Inflammatory Process and the Inflammatory Mediators," *Pharmacology & Toxicology*, 75(2):1–3, 1994.

Marui et al., "Vascular Cell Adhesion Molecule–1 (VCAM–1) Gene Transcription and Expression are Regulated Through an Antioxidant–Sensitive Mechanism in Human Vascular Endothelial Cells," *J. Clin. Invest.*, 92(4):1866–1874, Oct. 1993.

Slowik et al., "Tumor Necrosis Factor Activates Human Endothelial Cells Through the p55 Tumor Necrosis Factor Receptor but the p75 Receptor Contributes to Activation at Low Tumor Necrosis Factor Concentration," *Am. J. Pathol.*, 143(6):1724–30, Dec. 1993.

Springer et al., "Adhesion Receptors of the Immune System," *Nature*, 346(6283):425–434, Aug. 1990.

Tozawa et al., "Effects of Anti–Nuclear Factor Kappa B Reagents in Blocking Adhesion of Human Cancer Cells to Vascular Endothelial Cells," *Cancer Research*, 55(18):4162–4167, 1995.

Wellicome et al., "A Monoclonal Antibody that Detects a Novel Antigen on Endothelial Cells that is Induced by Tumor Necrosis Factor, IL–1, or Lipopolysaccharide," *J. Immunol.*, 144(7):2558–2565, 1990.

International Search Report dated Sep. 18, 1996.

Bevilacqua et al., "Endothelial Leukocyte Adhesion Molecule 1: An Inducible Receptor for Neutrophils Related to Complement Regulatory Proteins and Lectins," *Science*, 243:1160–1165, Mar. 1989.

SEQUENCE LISTING (1) GENERAL INFORMATION:

(iii) NUMBER OF SEQUENCES: 2

(2) INFORMATION FOR SEQ ID NO:1:

```
        (i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:1:

GGGGATTTCC                                                                        10

(2) INFORMATION FOR SEQ ID NO:2:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:2:

AGCTTAGAGG GGATTTCCGA GAGGA                                                       25
```

METHODS AND COMPOSITIONS FOR TARGETING SELECTINS

The U.S. Government owns rights in the present invention pursuant to grant number 58508 from the National Institutes of Health.

BACKGROUND OF THE INVENTION

1. Field of the Invention

The present invention relates generally to the fields of blood vessels and to radiation biology. More particularly, it provides a variety of compositions and methods for use in targeting the E-selectin or L-selectin marker following its specific induction in tumor vasculature endothelial cells, and for delivering selected therapeutic and diagnostic agents to the tumor vasculature.

2. Description of the Related Art

Although significant effort continues to be applied to the development of effective anti-cancer strategies, many prevalent forms of human cancer still resist effective chemotherapeutic intervention. A considerable underlying problem that must be addressed in any treatment regimen is the concept of "total cell kill." This is based on the fact that in order to have an effective treatment regimen, whether it be a surgical or chemotherapeutic approach, or both, all of the so-called "clonogenic" malignant cells must be killed to prevent regrowth of the tumor mass.

Due to the need to develop therapeutic agents and regimens capable of achieving such total cell kill, certain types of tumors have been more amenable than others to therapy. For example, lymphomas, and tumors of the blood and blood-forming organs, e.g., leukemias, have generally been more responsive to chemotherapeutic therapy, while solid tumors, such as carcinomas, generally prove more resistant to such therapies.

One underlying reason for this phenomenon is that blood-based tumors are physically more accessible to the chemotherapeutic agents, whereas it is often difficult for most chemotherapeutic agents to reach all of the cells of a solid tumor. Increasing the dose of chemotherapeutic agents, rather than achieving the desired total cell kill, most often results in toxic side effects that limit the effectiveness the chemotherapy.

Even immunotoxins, that are directed to selected cancer cell antigens, have proven to be of limited use in the treatment of solid tumors (Weiner et al., 1989; Byers et al., 1989). One reason for this is that solid tumors are generally impermeable to antibody-sized molecules, often exhibiting specific uptake values of less than 0.001% of the injected dose/g of tumor in human studies (Sands et al., 1988; Epenetos et al., 1986).

Further significant problems that can apply to any conventional chemotherapeutic include: the formation of mutants that escape cell killing and regrow; the dense packing of cells within the tumor that creates a physical barrier to macromolecular transport; the absence of lymphatic drainage, creating an elevated interstitial pressure that reduces extravasation and fluid convection; the heterogeneous distribution of blood vessels that leaves certain tumor cells at a considerable diffusion distance; and the adsorption of agents in the perivascular tumor cells.

It is therefore clear that a significant need exists for the development of novel strategies for the treatment of solid tumors. One approach involves the targeting of agents to the vasculature of the tumor, rather than to tumor cells. As solid tumor growth is dependent on the vascularization of the tumor to supply oxygen, nutrients and other growth factors, vascular-mediated mechanisms of action appear attractive. Also, in targeting the vasculature, the cells are generally accessible and the outgrowth of mutant endothelial cells, lacking a target antigen, is unlikely because they are normal cells.

For tumor vascular targeting to succeed, it is generally accepted that markers must be identified that are specific for tumor vascular endothelial cells and that are not significantly expressed in such cells in normal tissues. The failure to identify or develop appropriately effective markers has generally limited the development of the initially promising anti-vascular strategies.

SUMMARY OF THE INVENTION

The present invention seeks to overcome these and other drawbacks inherent in the prior art by providing improved methods and compositions for use in specifically targeting tumor vasculature endothelial cells, thereby delivering selected therapeutic and diagnostic agents to the tumor vasculature. The invention requires the induction of the molecule E-selectin or L-selectin in tumor vasculature endothelial cells, as may be achieved using ionizing radiation, which then allows E-selectin to be targeted using specific binding compositions and selected agents.

The invention therefore provides methods for delivering a selected agent to the vasculature of an animal or human subject comprising, generally, inducing E-selectin or L-selectin expression in vascular endothelial cells and administering to the animal a composition comprising an E-selectin or L-selectin targeting component operatively associated with or attached to a selected agent.

Also provided are methods for delivering a selected agent to the tumor-associated vasculature of an animal or human patient having a vascularized tumor, which methods generally comprise inducing E-selectin or L-selectin expression in the tumor-associated vascular endothelial cells and administering to the animal a composition comprising an E-selectin or L-selectin targeting compound operatively associated with or attached to a selected agent.

Further provided are methods for delivering a selected agent to the disease-associated vasculature of an animal or human subject with a disease that has a vascular component, i.e., a disease that is connected in some manner with the aberrant function, or number, of blood vessels. These methods generally comprise inducing E-selectin or L-selectin expression in the disease-associated vascular endothelial cells and administering to the animal or patient a composition comprising an E-selectin or L-selectin targeting compound operatively associated with a selected agent.

Methods for treating malignant and benign diseases that have a dysfunction of the vasculature as one causal or contributory factor are also provided. Such diseases include various solid tumors, diabetic retinopathy, vascular restenosis, arteriovenous malformation (AVM) and meningioma. These treatment methods generally include inducing E-selectin or L-selectin expression in the disease-associated vascular endothelial cells of an animal or patient having a vascularized tumor, or a vascular component-associated benign disease, and administering to the animal or patient a therapeutically effective amount of a pharmaceutical composition comprising an E-selectin or L-selectin targeting component operatively associated with or attached to a selected agent.

In all such methods of the invention, the E-selectin or L-selectin expression in vascular endothelial cells may be induced by ionizing radiation, i.e., by exposing the cells to ionizing radiation at a dose sufficient to activate the selectin promoter and to induce expression of the selectin structural gene so that the selectin protein is expressed on the surface of the cell.

E-selectin or L-selectin expression in vascular endothelial cells may be induced by γ-irradiation, or preferably, by using by x-rays. Where cancer or other disease are to be treated, E-selectin or L-selectin gene expression in the vascular endothelial cells may be induced by specific x-ray irradiation of the tumor or disease site.

Induction of E-selectin or L-selectin may also be achieved using heat or oxidants, such as $H_2O_2$ or $O_2$. This may also be controlled and directed to a specific area of the body.

Following E-selectin or L-selectin expression in the vascular endothelial cells, a composition of one or more selectin-second agent components is administered to the animal or patient, generally in a pharmaceutically acceptable formulation. This may be achieved by parenteral administration, by injection or instillation into the disease site or vascularized tumor site, e.g., using any one of a variety of catheters.

The E-selectin or L-selectin targeting component of the composition may be an antibody, preferably, a monoclonal antibody, or a fragment thereof, such as an scFv, Fv, Fab', Fab or $F(ab')_2$ fragment of an antibody. Preferred antibodies are monoclonal antibodies (MAbs), as may be obtained from a variety of commercial sources, e.g., British Biotechnology Ltd., R & D Systems, AMA Inc. and Imunotech S.A., or that may be generated using standard MAb technology.

Further suitable MAbs are those described in the scientific literature, such as EL-246 (Jutila et. al., 1992; Steinberg et al., 1994); 1.2B6 (Groves et. al., 1991; Montefort et. al., 1992; Moughal et. al., 1992; Keelan et al., 1994a; 1994b; Chapman et al., 1994); BBAI (Zhang et al., 1994); 9H9 (Olofsson et al., 1994); CL2/6 (Abbassi et. al., 1993); 1.3B6 (Veale et. al., 1993); BB11 (Sporn et. al., 1993); CL-3 and CL-37 (Mulligan et. al., 1991); ENA1 (Span et al., 1991; von Asmuth et. al., 1992); and ENA2 (Hakkert et. al., 1991).

Other effective E-selectin or L-selectin targeting components are oligosaccharides, polysaccharides, glycolipids, and even glycoproteins; oligosaccharides, polysaccharides or glycolipids formulated into liposome preparations; and oligosaccharides, polysaccharides or glycolipids conjugated to a protein or polypeptide carrier, such as albumin. Currently preferred liposome preparations are cationic liposomes, DOTMA/DOPE, DOTMA and DORIE.

Suitable oligosaccharides include glycyrrhizin, carminic acid, cylexin, sialyl Lewis X/A oligosaccharides and sialyl Lewis X/A mimics. Examples of sialyl Lewis X/A oligosaccharides include sialyl Lewis X (sialyl $Lewis^x$, $sLe^x$, Neu5Acα2-3Galβ1-4[Fucα1-3]GlcNAc); sialyl Lewis A (sialyl $Lewis^a$, $sLe^a$, Neu5Acα2-3Galβ1-3[Fucα1-4] GlcNAc); sialyl Lewis X/A ($sLe^{x/a}$); sialyl Lewis pentasaccharides; sialyl Lewis tetrasaccharides; sulfated Le penta- and tetrasaccharides; and dimeric sialyl Lewis compounds.

Currently preferred oligosaccharides are glycyrrhizin and sialyl Lewis X/A-based oligosaccharides, particularly sialyl Lewis pentasaccharides and tetrasaccharides; sulfated Le penta- and tetrasaccharides; and amino substituted $sLe^a$, as described by Nelson et. al. (1993).

Further useful E-selectin binding agents include structural analogues of the above oligosaccharides, including those identified in the pharmacophore search by Narasinga Rao et al. (1994).

Suitable E-selectin-binding polysaccharides include polylactosamine. A glycoprotein contemplated for use as an E-selectin targeting component is Protein C (Grinnell et. al., 1994); and the 150-kD, 230 kD and 130 kD glycoproteins described by Lenter et. al. (1994) may also be employed.

Further suitable E-selectin or L-selectin targeting components are viruses, such as herpes simplex virus-1 (HSV-1), adeno-associated virus (AAV), retroviruses, human papilloma virus (HPV) and adenoviruses. The currently preferred viruses for use in the present invention are HSV-1 and adenoviruses.

Still further effective E-selectin or L-selectin targeting components are cells, such as T lymphocytes or leukocytes, helper T cells, polymorphonuclear neutrophils, eosinophils, NK cells, and the like, that are known to bind to E-selectin and L-selectin physiologically. Tumor-infiltrating lymphocytes (TILs) may be obtained from the animal to be treated and re-administered in conjunction with a selected agent or transfected with the ELAM ligand fucosyltransferase (ELFT) gene. The selected agent may be a recombinant vector that is inserted into the TIL, so that the vector expresses a protein following uptake into the vascular endothelial cells.

Ligands isolated from T cells or from polymorphonuclear neutrophils, or recombinant versions of such ligands, may also be used as E-selectin or L-selectin targeting components. One such example is the HECA-452 antigen from lymphocytes (De Boer et. al., 1994).

Antibodies and oligosaccharide-containing compounds already administered to humans in the treatment of distinct diseases conditions may be initially preferred for use in this invention. For example, glycyrrhizin is a natural product that is used in Chinese herbal medicines (Davis and Morris, 1991). Many antibodies have been tested in animal models in studies directed to areas of diagnosis or treatment other than those connected with radiation (Keelan et al., 1994a; 1994b; Chapman et al., 1994; Ulich et al., 1994; Silber et al., 1994; Gosset et al., 1995), and as such have demonstrated acceptable safety levels. Diagnosis and therapy using antibody-based comounds is particularly based upon Roeske et. al. (1990) and Leichner et. al. (1993).

In the methods of the invention, after E-selectin or L-selectin expression is induced in vascular endothelial cells, a composition comprising a selectin targeting component operatively associated with, or attached to, a selected agent, is administered to an animal or patient.

Appropriate selected agents include therapeutic agents, such as thrombolytic agents, and also, anticellular agents that kill or suppress the growth or cell division of disease-associated endothelial cells. Examples of effective thrombolytic agents are streptokinase and urokinase.

Effective anticellular agents include classical chemotherapeutic agents, such as steroids, antimetabolites, anthracycline, vinca alkaloids, antibiotics, alkylating agents, epipodophyllotoxin and anti-tumor agents such as neocarzinostatin (NCS), adriamycin and dideoxycytidine; mammalian cell cytotoxins, such as interferon-α (IFN-α), interferon-βγ (IFN-βγ), interleukin-12 (IL-12) and tumor necrosis factor-α (TNF-α); plant-, fungus- and bacteria-derived toxins, such as ribosome inactivating protein, gelonin, α-sarcin, aspergillin, restrictocin, ribonucleases, diphtheria toxin, Pseudomonas exotoxin, bacterial endotoxins, the lipid A moiety of a bacterial endotoxin, ricin A chain, deglycosylated ricin A chain and recombinant ricin A chain; as well as radioisotopes.

Diagnostic agents will generally be a fluorogenic, paramagnetic or radioactive ion that is detectable upon imaging.

Examples of paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III) ions.

Examples of radioactive ions include iodine$^{123}$, technicium$^{99m}$, indium$^{111}$, rhenium$^{188}$, rhenium$^{186}$, copper$^{67}$, iodine$^{131}$, yttrium$^{90}$, iodine$^{125}$, astatine$^{211}$, gallium$^{67}$, iridium$^{192}$, cobalt$^{60}$, radium$^{226}$, gold$^{198}$, cesium$^{137}$ and phosphorus$^{32}$ ions. Examples of fluorogenic agents include gadolinium and renographin.

In operatively attaching a fluorogenic, paramagnetic or radioactive ion to an oligosaccharide, polysaccharide or glycolipid, one may wish to first conjugate the oligosaccharide, polysaccharide or glycolipid to a protein or polypeptide carrier, such as albumin, and then link the fluorogenic, paramagnetic or radioactive ion to the protein or polypeptide carrier, using methods commonly known in the art.

In certain embodiments, the selected agent will be a recombinant vector, or other gene-expressing unit, that comprises a promoter operatively linked to a protein expression region. The vector will then direct the expression of the encoded protein or polypeptide following uptake into vascular endothelial cells.

The recombinant vectors may comprise an ionizing radiation-inducible promoter, such as a CArG domain of an Egr-1 promoter, a fos promoter, a c-jun promoter or TNF-α promoter, operatively linked to a protein expression region. Alternatively, the vector may have a vascular endothelial cell specific promoter operatively, such as an Egr-1 gene promoter, an ICAM-1 gene promoter or an E-selectin gene promoter, linked to a protein expression region. Certain ionizing radiation-inducible promoters are also vascular endothelial cell specific promoters.

The protein expression region will often be one that expresses an anticellular agent capable of killing or suppressing the growth or cell division of disease-associated endothelial cells. Such agents are exemplified by tumor suppressor proteins, such as p53, p16, the retinoblastoma gene product and the Wilms' tumor gene product (WT1); chemotherapeutic agents, such as IFN-α, IFN-βγ, IL-12 and TNF-α; mammalian cell-, plant-, fungus- and bacteria-derived toxins, such as TNF-α, diphtheria toxin, Pseudomonas exotoxin, ricin A chain and deglycosylated ricin A chain; and agents that suppresses neovascularization.

The protein expression unit, gene or vector may also ultimately effect cell killing or growth suppression by expressing an enzyme capable of converting a non-toxic pro-drug into a cytotoxic drug. Effective examples include the herpes simplex virus (HSV) thymidine kinase (tk) enzyme and the cytosine deaminase enzyme.

The recombinant vector selected agents may be housed within cells, liposomes or viruses, such as a retrovirus, AAV, HSV-1, HPV, or adenovirus, or may be targeted to selectin-expressing cells via other means, such as by linking to an antibody.

The present invention further provides methods for delivering agents to cells, and for treating benign and malignant diseases. These methods generally comprise administering to an animal or patient in which vascular endothelial cell E-selectin or L-selectin expression has been induced, a pharmaceutical composition comprising an E-selectin or L-selectin targeting component operatively associated with a recombinant vector comprising an ionizing radiation-inducible promoter operatively linked to a protein expression region, and wherein the method further comprises inducing expression of the encoded protein by subsequently exposing the disease or tumor site to an additional effective dose of ionizing radiation.

The invention still further provides methods for determining the radiation exposure of an animal or patient, which methods generally comprise determining the level of E-selectin or L-selectin expression in vascular endothelial cells of an irradiated site of the animal or patient, wherein an increase in the E-selectin or L-selectin level, in comparison to the level in normal or non-irradiated animals or patients, is indicative of an increase in radiation exposure.

The level of selectin expression may be determined by means of administering to the animal or patient an effective amount of composition comprising an E-selectin or L-selectin targeting component operatively associated with a detectable marker and exposing the animal or patient to a detection device to identify the detectable marker.

The detection methods are exemplified by administering to the animal or patient glycyrrhizin, or an antibody that specifically binds to E-selectin or L-selectin, operatively associated with a nuclear magnetic spin-resonance isotope or a radioactive substance.

In yet further embodiments, the present invention concerns methods for preventing or treating radiation damage in an animal or human patient undergoing radiotherapy, or one that is accidentally exposed to ionizing radiation. These methods generally comprise administering to the irradiated animal or patient a pharmaceutically acceptable composition comprising an E-selectin or L-selectin targeting agent alone, without a selected or second agent. The pharmaceutically acceptable composition may be administered to the animal in a topical, oral or parenteral formulation, depending on the damaged or protectable area.

Compositions and kits of the present invention include all the above described combinations of E-selectin or L-selectin targeting components operatively associated with or attached to all the above described selected agents, and such compositions dispersed in pharmacologically acceptable media. Currently preferred E-selectin or L-selectin targeting components are antibodies, glycyrrhizin, carminic acid, cylexin, sialyl Lewis X, sialyl Lewis A, sialyl Lewis X/A and sialyl Lewis X/A mimics. Currently preferred selected agents are anticellular agent capable of killing or suppressing the growth or cell division of tumor-associated endothelial cells and fluorogenic, paramagnetic and radioactive ions that are detectable upon imaging.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-1, FIG. 1A-2, FIG. 1A-3, FIG. 1A-4, FIG. 1A-5, FIG. 1A-6 and FIG. 1B, HUVEC and HMEC cells were grown to 90% confluence, and incubated with primary IgG$_1$ antibody (mouse anti-human ICAM-1 and E-selectin-1, R&D Systems) for 20 min at 4° C. The cells were then rinsed and incubated with FITC-conjugated secondary antibody (goat anti-mouse IgG$_1$). FACS (Becton Dickinson) analysis was utilized for quantitation of receptor expression of ICAM-1 and E-selectin on HUVEC.

In FIG. 1A-1, FIG. 1A-2, FIG. 1A-3, FIG. 1A-4, FIG. 1A-5 and FIG. 1A-6, these fluorescence data were expressed as histograms of events versus log fluorescence and analyzed in comparison to the autofluorescence of unlabeled cells as well as the fluorescence of baseline ICAM-1 labeled or E-selectin-1-labeled cells as appropriate. The percentage shift of log fluorescence was calculated for quantitation of cells binding the antibody to CAMs after irradiation (10 Gy).

In FIG. 1B, HUVEC cells were irradiated with 10 Gy and incubated with the indicated antibodies at 2 h intervals.

FIG. 2. Deletion analysis of the E-selectin promoter in irradiated endothelial cells. HMEC grown to 90% confluence were cotransfected with a plasmid containing a CMV promoter linked to the β-galactosidase gene (1 µg), 12 µg of carrier DNA plasmids, and pE-sel(−587+35)GH or pE-sel (−587+35)GH ΔNFkB (5 µg), by use of Lipofectin reagent. Transfected cells were incubated for 16 h after transfection followed by treatment with 10 Gy (1 Gy/min, GE Maxitron) ionizing radiation, TNF or IL-1. Aliquots of the medium were assayed for growth hormone by ELISA. The cells were harvested by scraping at 36 h and lysed, and β galactosidase levels were quantified to normalized for transfection efficiencies. HMEC transfected with the E-selectin promoter (−578 to +35) linked to the growth hormone reporter gene. HMEC transfected with deletion mutation of the E-selectin NFkB binding site (5'-AGCTTAGAGG GGATTTCCGA GAGGA-3'; SEQ ID NO:2) (pE(−578)-GHΔkB) linked to the growth hormone reporter gene.

FIG. 3. NFkB binding activity in irradiated endothelial cells. In FIG. 3, primary cultures of HUVEC were pooled (3 umbilical veins) and passaged 3 times prior to irradiation. Nuclear extracts were prepared according to previously described methods (Schreiber et al., 1989) at 10, 20, 30, and 60 min after irradiation. The E-selectin NFkB binding sequence (5'AGCTTAGAGG GGATTTCCGA GAGGA-3'; SEQ ID NO:2) was end-labeled with a[$-^{32}$P]ATP by use of polynucleotide kinase.

In FIG. 3, binding assays were performed by incubating the end-labeled DNA (1 ng) with poly (dI-dC) in a 25 µl reaction for 20 min at room temperature. Competition studies were performed with oligonucleotides corresponding to known cis-acting elements, E-selectin NFkB (5'AGCTTAGAGG GGATTTCCGA GAGGA-3'; SEQ ID NO:2) and AP-1 (BRL-GIBCO) at a 100-fold molar excess as compared to the labeled fragments.

FIG. 4. PKC and PLA2 inhibition prior to x-ray-mediated E-selectin induction. The PKC inhibitors H7 and staurosporin or the PLA2 inhibitor BPB were added one h prior to irradiation. After irradiation, cells were scraped, and E-selectin was quantified by antibody labeling and FACS scanning.

FIG. 5. The Raf-1 kinase dominant negative (Raf 301) prevents transcriptional activation of the E-selectin promoter. HMEC were cotransfected with pE (−578)-GH, CMV-LacZ, and Raf 301 expression vector with the Lipofectin reagent. Transfectants were irradiated (10 Gy) or treated with TNF at 5 ng/ml. hGH was assayed by ELISA aliquots of medium at 8 and 24 h after treatment. The Raf 301 in antisense orientation to the promoter (Raf 302) served as a control. Transfections, treatment, and assays were performed simultaneously and under identical conditions to Raf 301 transfectants.

DETAILED DESCRIPTION OF THE PREFERRED EMBODIMENTS

Figures 1, 1A:
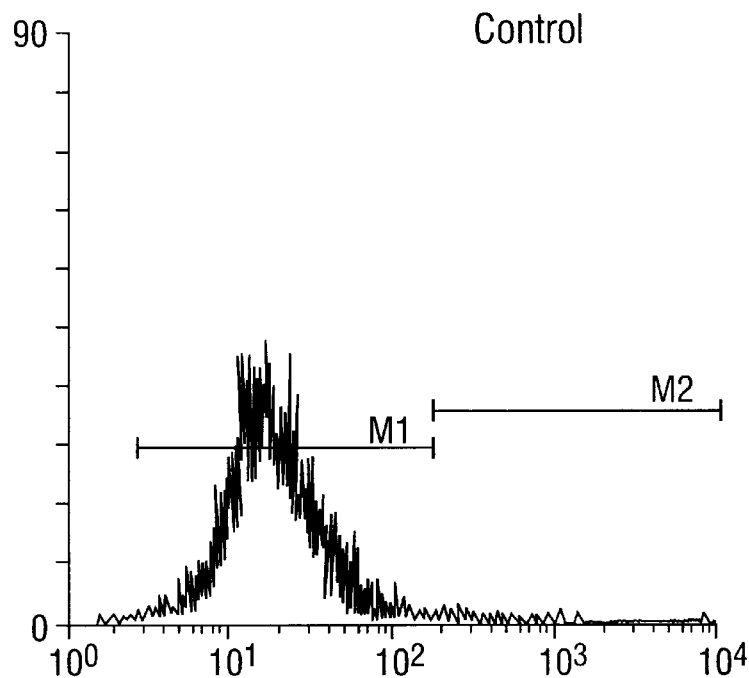
FIG. 1A-1, FIG. 1A-2, FIG. 1A-3, FIG. 1A-4, FIG. 1A-5, FIG. 1A-6 and FIG. 1B. Quantification of adhesion molecules in irradiated endothelial cells.

Persistent disease or local recurrence is a primary mode of failure in cancer patients, especially those with advanced disease (Haagense, 1971). For example, when breast tumors greater than 5 cm are treated with 80 to 90 Gy, 44% fail within the field of irradiation (Fletcher and Shukovsky, 1975). Furthermore, 50% of inflammatory breast carcinoma patients have local recurrences when the treated with daily irradiation (Barker et al., 1980), while twice daily irradiation combined with chemotherapy reduces the rate of local recurrence to 20 to 27% (Fastenberg, 1985).

Thus, improved local control has been achieved by aggressive chemotherapy and radiotherapy, but this is limited by both local and systemic toxicity. Systemic toxicities may be reduced and efficacy may be increased by localizing therapy to the site of disease. One approach to localizing anticancer pharmaceuticals to cancers is to use cytotoxic agents with an affinity for tumor vasculature (Bicknell, 1994). The vasculature is required for neoplasia and destruction of the vasculature can result in tumor necrosis (Malik, 1992). Carcinomas have abundant vasculature that may serve as a target for site specific anticancer pharmaceuticals (Harris et al., 1994).

Endothelial cells line the lumen of blood vessels and cell adhesion-molecules (CAMs) expressed on their surface represent a potential target for "site-directed" pharmaceuticals. CAMs influence neutrophil binding following stimulation with cytokines or oxidants (Read et al., 1994; Bevilacqua et al., 1989). CAMs can also be induced by viral infection (Etingin et. al., 1991). As CAMs bind to specific carbohydrates, glycoproteins, cells, viruses and antibodies, they represent a potential target for therapeutics.

The inventors contemplated that an improved means of localizing CAM-based pharmaceuticals is to induce expression of a CAM within the tumor volume. This would require a CAM that is readily inducible, but has no basal expression in unirradiated tissues. The inventors selected low dose ionizing radiation as the inducing agent to promote endothelial cell surface expression of candidate molecules, with the aim of using radioisotopes and stereotactic radiotherapy to induce expression of CAMs in the vasculature of advanced cancers.

The findings that acute and subacute clinical manifestations of ionizing radiation may in part mimic the inflammatory response to a number of stimuli (Slauson et al., 1976; Narayan and Cliff, 1982; Dunn et al., 1986) prompted the inventors to investigate this area. Neutrophil margination of the vasculature and infiltration of the perivascular region occurs rapidly following irradiation (Reinhold et al., 1990; Hopewell et al., 1993; Dunn et al., 1986; Matzner et al., 1988). One of the components of acute inflammation is enhanced adherence of leukocytes to the endothelium before extravasation (Cliff, 1966). During the inflammatory reaction, endothelial cells rapidly and transiently produce a number of glycoproteins that influence neutrophil binding (Pober and Cotran, 1990).

Examples of inducible glycoproteins expressed rapidly and transiently within the lumen of blood vessels include the selectins E-selectin and P-selectin, which have low constitutive expression and serve as receptors for neutrophils and lymphocytes (Montgomery et al., 1991; Ghersa et al., 1992; Swerlick & Lawley, 1993). Other adhesion molecules, such as ICAM-1 and VCAM-1, have higher constitutive expression that increase following exposure to cytokines. Prior to the inventors' work, it was unclear as to which, if any, of these potential targets would prove to be a useful target in a practical sense.

Because of the association between oxidant injury and expression of adhesion molecules on the surface of endothelial cells, the inventor quantified expression of E-selectin, VCAM, ICAM, P-selectin in irradiated endothelial cells. Primary culture HUVEC cells were expanded from single umbilical veins irradiated followed by fixation and incubation with antibodies to adhesion molecules (R & D systems). The percentage of cells binding the antibody to E-selectin increased from 1 to 3% in untreated controls to 15 to 32% at 4 h following irradiation. In comparison, there was no significant increase in the percentage of cells binding antibodies to P-selection or VCAM following irradiation. The percentage of cells binding the antibody to ICAM increased from 20 to 30% in untreated controls to 50 to 65% at 20 h following irradiation. In comparison, interleukin-1 was used as a positive control and increased the expression of each of the adhesion molecules by 20 fold for E-selection, 3 fold each for ICAM, VCAM and P-selectin.

To examine the time dependent increase in radiation-mediated adhesion molecule expression, HUVEC cells were irradiated with 10 Gy and incubated with antibody at 2 h intervals. The increase in E-selection expression began at 2 h, peaked at 4 to 6 h and gradually returned to baseline at 20 h. In contrast, ICAM expression remained at baseline levels until 16 h following irradiation and peak expression plateaued at 24 to 36 h following irradiation.

To study the dose dependence of x-ray-mediated adhesion molecule expression, HUVEC cells were irradiated with a dose range from 0.5 to 50 Gy and cells were scraped at 4 or 24 h. E-selectin expression increased at 4 h following exposure to 0.5 Gy and increased in a dose dependent manner until 20 Gy after which plateau was reached. When cells were scraped and incubated with antibody 24 h following irradiation, only cells treated with 20 Gy or greater had a persistent increase in E-selectin expression as compared to those treated with lower doses that returned to baseline. In contrast, ICAM was not expressed at x-ray doses below 5 Gy, but showed an increase at 24 h when treated with higher doses.

These data indicate that E-selectin is induced transiently following low doses of irradiation, while ICAM induction requires high radiation doses and expression is more prolonged and PCAM and VCAM are not increased by irradiation. The inventors also found that E-selectin induction in irradiated endothelial cells is PKC independent but requires the NFkB binding sequence and Raf-1 kinase activity.

Several classes of molecules bind to E-selectin including carbohydrates such as glycyrrhizin and sialyl Lewis X/A, monoclonal antibodies to E-selectin, and polymorphonuclear neutrophils. Conjugation of pharmaceuticals to molecules that bind E-selectin is now contemplated to allow localization of many classes of pharmaceuticals (Kanoka et al., 1990). These include chemotherapeutic agents, radiopharmaceuticals, and gene therapy delivery systems such as liposomes, and lysosomes. Moreover, preliminary results of gene therapy in the treatment of cancer have had encouraging results (Gutierrez et al., 1992), and can now be improved using E-selectin-targeting agents.

This invention therefore provides E-selectin conjugated pharmaceuticals that are directed to locally advanced cancers following radiation-induction of E-selectin. The invention is also intended for use in benign neoplasms, including meningiomas, arteriovenous malformations, hemangiomas and the like. Additionally, the invention may be employed in the treatment of other vascular diseases, such as diabetic retinopathy, because these treatments will destroy the aberrant vasculature—as the presently used laser treatment does.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

E-selectin Induction in Endothelial Cells by Ionizing Radiation

This example shows that when the human endothelial cells HUVEC and HMEC are exposed to ionizing radiation, they exhibit dose and time-dependent increases in the endothelial leukocyte adhesion molecule E-selectin, in the absence of changes in VCAM-1, P-selectin and GMP 140 protein levels.

The acute and subacute clinical manifestations of ionizing radiation mimic the inflammatory response to a number of stimuli. For example, radiation-induced pneumonitis, cystitis, mucositis, esophagitis and dermatitis each demonstrate inflammation as a predominant component (Slauson et al., 1976; Dunn et al., 1986; Ward et al., 1993). Furthermore, ionizing radiation is associated with neutrophilic vasculitis and interstitial inflammation (Narayan, 1982; Slauson et al., 1976; Fajardo and Berthrong, 1988).

The pathophysiology of these sequelae is related to margination of neutrophils in the vasculature and infiltration of the perivascular region after irradiation (Reinhold et al., 1990; Hopewell et al., 1993; Dunn et al., 1986; Matzner et al., 1988). Increased adherence of neutrophils to endothelial cells occurs during acute pulmonary radiation injury (Slauson et al., 1976). Similarly, oxygen radicals also induce human endothelial cells to bind neutrophils (Patel et al., 1991).

Endothelial cells exposed to ionizing radiation respond in a manner analogous to that observed during acute inflammation. This response is associated with leukocyte margination and an increase in vascular permeability. These processes may account for the pathogenesis of radiation injury (Hopewell et al., 1993). An understanding of the pathophysiology of the radiation-mediated inflammatory response will facilitate pharmacologic intervention for these sequelae of radiation therapy.

Endothelial cells rapidly and transiently produce a number of glycoproteins that influence neutrophil binding during the inflammatory reaction (Pober and Cotran, 1990). The potential pathology associated with expression of these proteins on the surface of the endothelium is avoided by their virtual absence prior to stimulation with cytokines or oxidants (Read et al., 1994; Bevilacqua et al., 1989).

Examples of inducible glycoproteins expressed rapidly and transiently within the lumina of blood vessels include E-selectin and P-selectin which have low constitutive expression and serve as receptors for neutrophils and lymphocytes (Bevilacqua, 1993; Pober and Cotran, 1990). This highly restrained transcriptional regulation is in contrast to that of other adhesion molecules such as ICAM-1 and VCAM-1, which have higher constitutive expression that increases further after exposure to cytokines.

The transcriptional regulation of E-selectin is judiciously controlled (Montgomery et al., 1991; Ghersa et al., 1992) because of its pivotal role in the endothelial cell response during inflammation and hypoxia, whereas ICAM induction is regulated less vigorously. Due to the association between oxidant injury and the expression of adhesion molecules on the surface of endothelial cells, the inventors chose to quantify the expression of E-selectin, VCAM, ICAM, and P-selectin in irradiated endothelial cells. The inventors found that the expression of E-selectin and ICAM is increased following irradiation, in a time course analogous to that observed after stimulation with cytokine.

A. Materials and Methods

1. Cell Culture

Primary cultures of human umbilical vein endothelial cells (HUVEC) were prepared from fresh (<24 h old) human umbilical veins transported to the laboratory in sterile buffer at 4° C. The vein was cannulated, filled with 0.2% collagenase, and incubated at 37° C. for 15 min. Cells were flushed and complete medium was added, followed by centrifugation at 2000 rpm for 5 min; the supernatant was discarded. The cell pellet was resuspended and maintained in M199 with 10% fetal calf serum, 10% human serum, Pen/Strep/Amphotericin B solution (Sigma) on gelatin-coated (0.2%) tissue culture dishes at 37° C. in 5% $CO_2$. Confluent cells were subcultured with 0.1% collagenase 0.01% EDTA. Cells (HUVEC) were used at third passage; this reduced the number of passenger cells and allow for uniform expression of cellular adhesion molecules.

Endothelial cells from human dermis immortalized with SV40 (HMEC) (Ades et al., 1992) were maintained in endothelial basal medium MCDB131 (Gibco/BRL) supplemented with 15% FBS, 10 ng/ml epidermal growth factor (Collaborative Biomedical Products), 1 $\mu$g/ml hydrocortisone (Sigma), and Pen/Strep.

2. Quantification of adhesion molecules in irradiated endothelial cells

HUVEC and HMEC cells were grown to 90% confluence and irradiated with a GE Maxitron x-ray generator as previously described (Hallahan et al., 1989). Cells were removed from flasks with 0.1% collagenase, 0.01% EDTA, 0.25% BSA and pelleted in 12×75 mm polystyrene tubes. The supernatant was discarded and the cells were incubated with primary $IgG_1$ antibody (mouse anti-human ICAM-1 and E-selectin-1; R&D Systems, Inc., Minneapolis, MN) for 20 min at 4° C.

The cells were then rinsed with isotonic phosphate buffered saline (PBS), pelleted and incubated with FITC-conjugated secondary antibody (goat anti-mouse $IgG_1$) for 20 min at 4° C. The fluorescently labeled cells were rinsed in PBS and fixed in PBS containing 0.01% paraformaldehyde. Nonspecific binding was evaluated with the use of FITC-conjugated secondary antibody alone and with a lymphocyte specific first-step antibody, anti-$CD_{10}$, which does not bind to endothelial cells.

Fluorescence activated cell sorting (FACS) analysis was utilized for quantitation of receptor expression of ICAM-1 and E-selectin on HUVEC. The Becton Dickinson FACScanner was used with Lysis II software. Forward and side scatter fluorescence data identified 10,000 viable endothelial cells in each experimental group for unlabeled cells, nonspecific-antibody-labelled cells, ICAM-1-labeled cells and E-selectin-labeled cells. Fluorescence data were then accumulated on each group of 10,000 cells at 530 nm, the wavelength emitted by FITC.

The fluorescence data were expressed as histograms of events versus log fluorescence and analyzed in comparison to the autofluorescence of unlabelled cells as well as the fluorescence of baseline ICAM-1 labelled or E-selectin-1 labeled cells as appropriate. During inhibition studies, PKC inhibitors H7 100 nM and staurosporin 10 nM or Phospholipase A2 inhibitors BPB 10 $\mu$M or mepacrine 20 $\mu$M were added to cell cultures 30 min prior to irradiation.

3. RNA analysis

HUVEC cells were grown to 90% confluence and exposed to x-rays (10 Gy, GE Maxitron x-ray generator) as previously described (Hallahan, 1989). RNA was extracted with the single-step guanidinium thiocyanate-phenol/chloroform method (Chomczynski and Sacchi, 1987) at 1 h after irradiation. Control RNA was obtained from nonirradiated cells treated under otherwise identical conditions. RNA was size-fractionated by 1% agarose formaldehyde electrophoresis. Ethidium bromide staining of the RNA demonstrated equal loading of each lane. RNA gels were then transferred to a nylon membrane (Genescreen Plus, New England Nuclear). Northern blots were hybridized to $^{32}P$ labeled E-selectin cDNA (Collins et al., 1991) probe followed by autoradiography for 3 days at −85° C. with intensifying screens.

B. Results

1. Quantitation of adhesion molecules in irradiated HUVEC

To determine the effects of cell adhesion molecules, the inventors expanded primary culture HUVEC from single human umbilical veins that were irradiated, followed by fixation and incubation with antibodies to E-selectin, P-selectin, ICAM-1, and VCAM. The log fluorescence of cells incubated with the antibody to E-selectin shifted by 15 to 32% at 4 h after irradiation (FIG. 1A-1, FIG. 1A-2, FIG. 1A-3, FIG. 1A-4, FIG. 1A-5 and FIG. 1A-6). In comparison, the log fluorescence of cells incubated with the antibody to ICAM shifted by 30 to 35% at 20 h after irradiation (FIG. 1A-1, FIG. 1A-2, FIG. 1A-3, FIG. 1A-4, FIG. 1A-5 and FIG. 1A-6). However, there was no significant increase in P-selectin or VCAM protein expression following irradiation. Interleukin-1 (IL-1) as used as a positive control and shifted the log fluorescence for E-selectin by 43%, ICAM-1 (31%), VCAM-1 (25%), and P-selectin (30%). These data indicate that x-ray induction of CAM's is specific for E-selectin and ICAM whereas IL-1 induces all CAM's quantified.

To examine the time-dependent increase in the radiation-mediated expression of cell adhesion molecules, the inventors irradiated HUVEC with 10 Gy and incubated them with antibody at 2 h intervals after irradiation. E-selectin expression began to increase at 2 h, peaked at 4 to 6 h, and gradually returned to baseline at 20 h (FIG. 1B). In contrast, ICAM expression remained at baseline levels until 16 h after irradiation, and peak expression occurred at 24 to 36 h following irradiation.

HUVEC were then irradiated with doses ranging from 0.5 to 50 Gy and assayed at 4 or 24 h for study of the dose dependence of the x-ray-mediated expression of cell adhesion molecules. E-selectin expression increased at 4 h after exposure to 0.5 Gy and increased in a dose dependent manner up to 20 Gy, where a plateau was reached. When cells were assayed at 24 h following irradiation, only cells treated with 20 Gy or higher doses had a persistent increase in E-selectin expression, whereas those treated with lower doses approximated baseline expression. In contrast, ICAM expression was not increased at x-ray doses below 5 Gy, but demonstratable increases occurred at 24 h when treated with higher doses. These data indicate that E-selectin is induced transiently after low doses of irradiation, whereas ICAM induction requires high radiation doses and is sustained.

2. E-Selectin Gene Expression in Irradiated HUVEC

HUVEC cells were exposed to x-rays (10 Gy) and RNA was extracted at 1 h intervals after irradiation. Northern blots were hybridized to $^{32}$P labeled E-selectin cDNA (Collins, 1991) HUVEC cells were grown to 90% confluence and exposed to x-rays (10 Gy) and RNA was extracted at 1 h after irradiation. Control RNA was obtained from nonirradiated cells treated under otherwise identical conditions. RNA was size-fractionated by 1% agarose formaldehyde electrophoresis. Northern blots were hybridized to $^{32}$P labeled E-selectin cDNA. The deletion analysis of the E-selectin promoter in irradiated endothelial cells shows increased E-selectin RNA at 2 h after irradiation. Because increases in E-selectin are regulated at the level of transcription in response to cytokines and hypoxia/reoxygenation, the inventors transfected HUVEC or HMEC with the E-selectin promoter (−578 to +35) linked to the growth hormone reporter gene (pE (−578 to +35)-GH). Transfectants and control cells were irradiated with 10 Gy at 16 h after transfection with liposomes. Growth hormone from the medium of endothelial cells was quantified by ELISA at 24 and 48 h after irradiation.

Figures 1, 1A, 2:
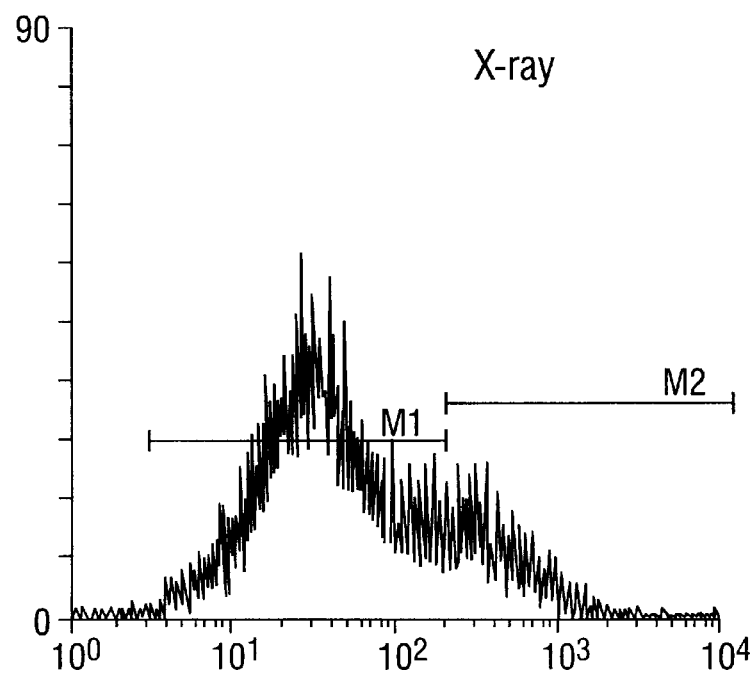

Cells transfected with plasmid pTK-GH demonstrated no radiation induction, whereas those transfected with plasmid pE (−578 to +35)-GH had a 7-fold (HUVEC) to 10-fold (HMEC) increase in expression after irradiation as compared to untreated controls (FIG. 2). HMEC and HUVEC transfected with the LacZ expression vector did not produce hGH after irradiation.

C. Results

Primary adhesion of leukocytes to the endothelium is an initial step in inflammation (Jones et al., 1995). To begin investigating this process in radiation-mediated inflammation, the inventors quantified adhesion molecules on endothelial cells after x-irradiation. The inventors found that E-selectin and ICAM-1 are induced by x-irradiation of human endothelial cells. The time course of expression of these gene products is analogous to that observed following stimulation with cytokines in that E-selectin increases after 4 h and is transient, whereas ICAM is induced after 20 h and is prolonged (Springer, 1994).

These results are supported by the finding that ICAM is induced by x-irradiation of tumor cell lines and human epidermal keratinocytes (Behrends et al., 1994). These adhesion molecules interact with oligosaccharides on the surface of leukocytes mediating the rolling of leukocytes in the microvasculature (Nelson et al., 1993; Jones et al., 1995). Thus, x-ray-mediated CAM expression in endothelial cells may play a role in the inflammatory effects of ionizing radiation.

The inventors propose that the clinical relevance of CAM induction by x-rays is that radiation-induced vascular injury may involve induction of E-selectin and ICAM within endothelial cells. This is supported by the association of reactive oxygen species in the development of atherosclerosis (Collins, 1993) and renal injury from radiation (Jaenke et al., 1993). In this regard, endothelial cells are continuously exposed to various forms of reactive oxygen species. For example, $H_2O_2$ and other oxygen radicals are produced by granulocytes and macrophages during inflammation and reoxygenation (Dowell et al., 1993).

In addition to the findings in this study, endothelial cells respond to ionizing radiation with the release of chemoattractants and eicosanoids (Eldor et al., 1989; Eldor et al., 1989). Furthermore, cytokines such as TNF and IL-1 are induced by x-rays (Hallahan et al., 1993). However, the inventors quantified these cytokines in irradiated endothelial cells using ELISA and found no induction. These processes are thought to result in the pathogenesis of organ injury following ionizing radiation exposure. The inventors now propose that vascular injury within irradiated tissues occurs through the activation of a local inflammatory response mediated by adhesion molecules as well as cytokines (Hallahan et al., 1989). The clinical implication of these findings is that CAM ligands (Nelson et al., 1993; Narasinga Rao et al., 1994) may be effective in the treatment or prevention of the inflammatory component of radiotherapy.

EXAMPLE II

The NFkB Sequence is Required for E-selectin Induction

This example shows that the NFkB binding site within the promoter region of E-selectin (−578 to +35) is required for x-ray induction of the E-selectin structural gene, and that the nuclear protein binds to the E-selectin-NFkB sequence.

The promoter region of E-selectin contains an NFkB binding region (Montgomery et al., 1991) which is necessary for induction following stimulation with tumor necrosis factor (TNF) (Whelan et al., 1991). NFkB rapidly activates gene expression during inflammation and the immune response. The NFkB motif in the E-selectin promoter (GGGGATTTCC; SEQ ID NO:1) is in agreement with the consensus sequence (GGRNTTTCC) for binding of p65 (Kunich et al., 1992).

NFkB is a multi-subunit transcription factor which is present in the cytoplasm while complexed to IkB and which consists of a p50 and p65 heterodimer. After appropriate phosphorylation reactions, NFkB translocates to the nucleus where it binds to an 11-base-pair sequence, GGRNTTTCC, to regulate expression of a number of genes (Pober and Cotran, 1990).

Affinity of NFkB for DNA binding is activated by many pathogenic agents including viral products, cytokines, hypoxia (Koong et al., 1994), reactive oxygen intermediates (ROIs) (Meyer et al., 1993) and radiation (Prasad et. al., 1994). The inventors therefore analyzed the role of NFkB activation following irradiation with x-rays. It was found that the NFkB binding region within the E-selectin promoter is required for transcriptional activation.

A. Materials and Methods

1. Nuclear Protein Analysis

Electrophoretic mobility shift assays of nuclear protein extracts from irradiated HUVEC cells at 90% confluence were performed as follows. Nuclear extracts were prepared according to previously described methods (Schreiber et al., 1989) at 10, 20, 30, and 60 min after irradiation. HUVEC cells ($10^6$) were washed in 10 ml PBS, scraped, and pelleted by centrifugation at 1500 g for 5 min and the cell pellet was resuspended in 400 μl of cold buffer A (10 mM HEPES, pH 7.9; 10 mM KCl; 0.1 mM EDTA; 1 mM DTT; 0.5 mM PMSF; 1 μg/ml leupeptin, and 5 μg/ml aprotinin).

The cells were allowed to swell on ice for 15 min, followed by the addition of 25 μl of 10% NP-40, and vortexed for 10 sec at high speed. The mixture was centrifuged for 30 sec and the nuclear pellet resuspended in 50 μl of ice-cold buffer B (20 mM HEPES, pH 7.9; 0.4 M NaCl; 1 mM EDTA; 1 mM DTT; 1 mM PMSF; 25% glycerol; 1 μg/ml leupeptin and 5 μg/ml aprotinin), homogenized, and rocked vigorously for 15 min. The nuclear extract was then centrifuged for 5 min. Protein content was determined by the Bradford method (Bio-Rad).

The E-selectin NFkB binding sequence (5'AGCTTAGAGGGG ATTCCG AGAGGA-3'; SEQ ID NO:2) was end-labeled with a[−$^{32}$P]ATP by use of polynucleotide kinase. Binding assays were performed by incubation of the end-labeled DNA (1 ng) with 10 μg of nuclear protein, 75 mM KCl, 250 mM NaCl, 5 mM DTT, 5 mM EDTA, 25-1-glycerol, and 2 μg/sample of poly (dI-dC) in a 25 μl reaction for 20 min at room temperature. Competition studies were performed with oligonucleotides corresponding to the known cis-acting elements E-selectin NFkB (5'AGCTTAGAGGGG ATTTCCG AGAGGA-3'; SEQ ID NO:2) and AP-1 (BRL-GIBCO) at a 100-fold molar excess as compared to the labeled fragments. The reaction products were separated by 6% nondenaturing polyacrylamide gel electrophoresis, dried and analyzed by autoradiography.

Gel supershift assays were performed as described above, with the exception that, subsequent to incubation of oligonucleotide probes with nuclear extracts, 2 μg of affinity purified rabbit polyclonal antibody raised against human NFkB p65 and p50 or 5 μl crude rabbit anti human c-rel (obtained from N. Rice; N.I.H.) was added to the reaction mixture and incubated for 15–30 min.

2. Analysis of Transcriptional Regulation

Plasmid pE-sel(−587+35)GH or pE-sel(−587+35)GH Δ (5 μg) was cotransfected with a plasmid containing a CMV promoter linked to the LacZ gene (1 μg) and 12 μg of carrier DNA into HMEC or HUVEC cells grown to 90% confluence by use of lipofection. The medium was changed to optiMEM, and cells were transfected with Lipofectin Reagent (BRL-GIBCO) for 8 h, followed by the addition of complete medium and incubation overnight. Transfectants were incubated for 16 h after transfection followed by treatment with 10 Gy (1 Gy/min, GE Maxitron) of ionizing radiation, and with TNF or IL-1. Aliquots of the medium were assayed for growth hormone by ELISA. The cells were harvested by scraping at 36 h, lysed, and β galactosidase levels were quantified in extracts to normalized transfection efficiencies. The means and standard errors of 3 studies are presented.

3. Enzyme linked immunosorbent assays

HUVEC and HMEC cells were grown to 90% confluence followed by treatment with 20 Gy (1 Gy/min, GE Maxitron) ionizing radiation. Aliquots of the medium were assayed for growth hormone by ELISA assay. The cells were harvested by scraping at 16 and 36 h and lysed, and TNF levels were quantified again by ELISA (R&D Systems). Human growth hormone was released into the medium. This was quantified by hGH ELISA (BRL-Gibco).

B. Results

1. NFkB is required for x-ray induction of E-selectin

The promoter region of E-selectin contains an NFkB binding region (Montgomery et al., 1991) which is necessary for induction of E-selectin after stimulation with TNF (Whelan et al., 1991). The NFkB motif in the E-selectin promoter (GGGGATTTCC; SEQ ID NO:1) is in agreement with the consensus sequence (GGRNTTTCC) for p65 binding (Kunich et al., 1992).

To determine the role of NFkB in E-selectin induction after irradiation, the inventors analyzed the effects of irradiation on transcription of the E-selectin with a deletion mutation of the E-selectin NFkB binding site (5'-AGCTTAGAGGGG ATTTCCG AGAGGA-3'; SEQ ID NO:2) (pE(−578) -GHΔkB). Endothelial cells transfected with plasmid pE(−578) -GHΔkB had a 0.9-fold (HUVEC) to 1.1-fold (HMEC) increase in expression after irradiation as compared to untreated controls (FIG. 2).

Figures 1, 1A, 2, 3:
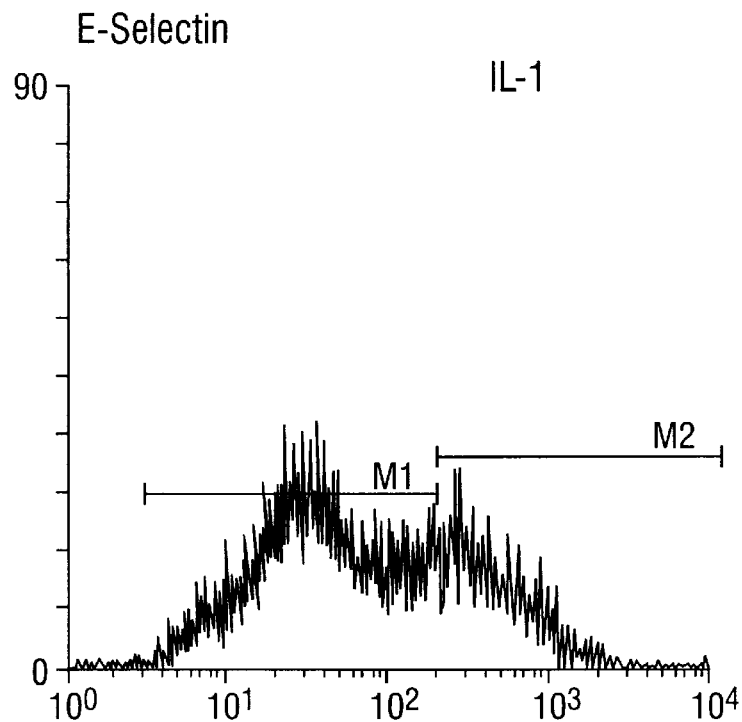

2. Nuclear Proteins from Irradiated Endothelial Cells Bind the E-selectin NFkB sequence To determine whether nuclear proteins bind to the E-selectin NFkB sequence after irradiation of endothelial cells, nuclear proteins were isolated at 15, 20, 25, 30, 45, and 60 min after irradiation of HUVEC. The end-labeled E-selectin NFkB binding site (5'-AGCTTAGAGGGG ATTTCCG AGAGGA-3'; SEQ ID NO:2) was incubated with nuclear protein extracts and separated by acrylamide gel electrophoresis (FIG. 3). This demonstrated increased binding of nuclear proteins to the labeled NFkB sequence, resulting in a banding pattern like that produced by treatment with IL-1 and TNF together.

Unlabeled (cold) E-selectin NFkB binding sequence was added to protein-labeled NFkB mixtures at 100- and 1000-fold excess, which prevented labeled DNA from binding as the mobility gel shift banding pattern was eliminated. Unlabeled (cold) AP-1 consensus sequence did not interfere with the protein-DNA interaction, indicating that this interaction is specific for NFkB (FIG. 3).

Because the mobility gel shift banding pattern following x-irradiation resembles that following stimulation with IL-1 and TNF and because these cytokines activate p65 and p50 binding to the NFkB consensus sequence, the inventors studied the role of these nuclear proteins in radiation-mediated E-selectin induction.

To determine which of the kB binding proteins participates in binding to the E-selectin NFkB binding site (5'-AGCTTAGAGGGG ATTTCCG AGAGGA-3'; SEQ ID NO:2), the inventors added antibodies to human p50, p65, and c-rel to nuclear protein/DNA mixtures. Gel supershift assays were performed as described in the brief description of the drawings, except that, subsequent to incubation of oligonucleotide probes with nuclear extracts, affinity-purified rabbit polyclonal antibody raised against human NFkB p65 and p50 or 5 (mu)1 crude rabbit anti-human c-rel were added to the reaction mixture. Nuclear protein extracts incubated with p50 and p65 antibodies produced a supershift in the mobility gel shift assay, whereas c-rel antiserum did not shift the banding pattern). Antibodies to Jun and Fos were selected because the inventors had previously shown that these transcription factors are activated by x-rays (Hallahan et al., 1992). These antibodies did not alter the banding pattern of the mobility gel shift, indicating that this was not a nonspecific protein-DNA interaction.

C. Discussion

NFkB is both an important mediator of the cellular response to ionizing radiation and participates in transcriptional regulation of adhesion molecules. The inventors investigated the role of NFkB activation in transcriptional regulation of E-selectin within irradiated endothelial cells. Similar observations were made in lymphoblastoid cells after irradiation (Brach et al., 1991).

NFkB is activated by $H_2O_2$, whereas activation by other stimulants is prevented by antioxidants (Schreck et al., 1991; Meyer et al., 1993). Oxidant activation of NFkB does not occur directly (Schreck et al., 1992), but metabolism of $H_2O_2$ or intracellular reactions such as oxidation of membrane lipids are first required. Phospholipase A2 activation may play an important role in the initiation of signal transduction within cells exposed to oxidants (Gustafson et al., 1991). In the present study however, phospholipase A2 inhibitors did not prevent NFkB activation and subsequent E-selectin induction in irradiated endothelial cells.

The role of ROIs in NFkB activation is demonstrated by NAC and PDTC, which block the activation of NFkB by a number of agents, including cycloheximide, double stranded RNA, calcium ionophore, TNF, phorbol esters, IL-1, LPS and lectins (Ziegler et al., 1993). Taken together with findings in the present study, NFkB plays a major role in signaling following exposure of endothelial cells to ROIs.

EXAMPLE III

Raf-1 Kinase is Necessary for X-ray Induction of E-selectin

Using the methods described in Example I and Example II, the present example shows that the dominant negative Raf-1 kinase (raf-301) blocks x-ray induction of the E-selectin promoter.

NFkB in the cytoplasm is complexed to IkB. IkB phosphorylation and dissociation from NFkB is dependent upon signal transduction through protein kinase C (PKC) or Raf-1 kinase pathways (Li and Sedivy, 1993; Finco and Baldwin, 1993). NFkB subsequently translocates to the nucleus where it regulates gene expression. The inventors analyzed the role of NFkB activation following x-ray-mediated PKC activation, and found E-selectin promoter activity to be PKC-independent.

Figures 1, 1A, 2, 3, 4:
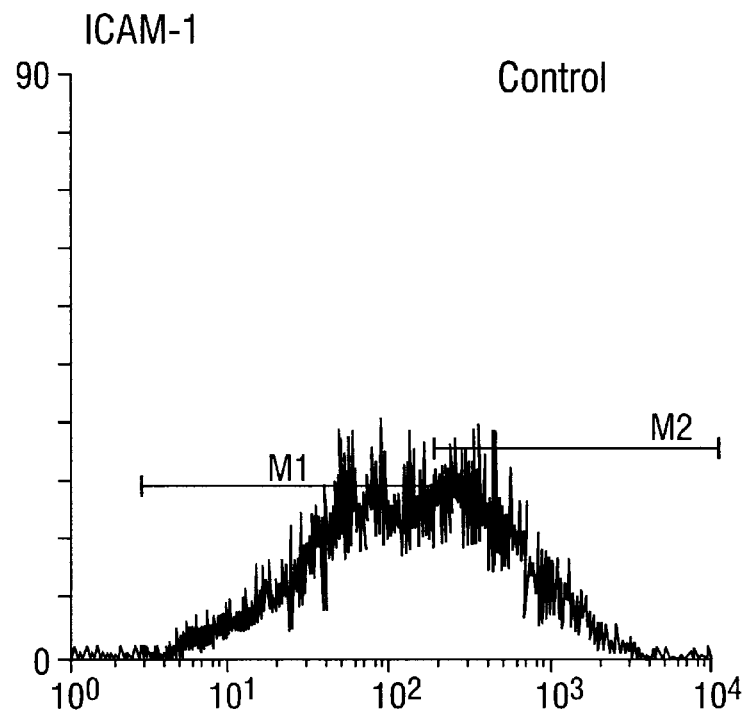

1. PKC and PLA2 inhibition does not influence x-ray-mediated E-selectin induction PKC participates in both NFkB activation and signal transduction initiated by ionizing radiation (Hallahan et al., 1991). Furthermore, PLA2 participates in free-radical and x-ray-mediated PKC activation and gene induction (Hallahan et al., 1991). To determine whether PLA2 or PKC activation is required for radiation-mediated E-selectin induction, the inventors added the PKC inhibitors H7 and staurosporin or the PLA2 inhibitors BPB or mepacrine to HUVEC one h prior to irradiation. Following irradiation, cells were scraped and E-selectin was quantified by antibody labeling and flow cytometry. Radiation-mediated E-selectin production was not attenuated by pretreatment with inhibitors (FIG. 4).

2. The Raf-1 kinase dominant negative (Raf 301) prevents transcriptional activation of the E-selectin promoter The Raf-1 kinase-dependent signaling pathway is activated by ionizing radiation, independent of PKC, and participates in NFkB activation. One means of specifically analyzing the role of Raf-1 kinase is the use of the Raf-1 dominant negative (Raf 301) (Porras et al., 1994) with a mutation at the ATP binding site which binds substrate but does not phosphorylate. When overexpressed, Raf 301 competitively inhibits the function of the wild-type enzyme.

Figures 1, 1A, 2, 3, 4, 5:
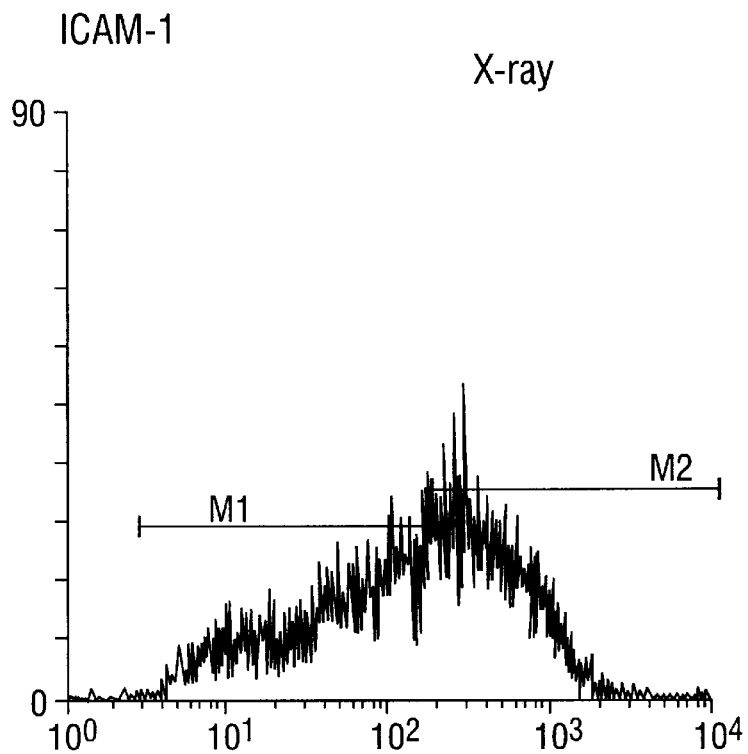
Figures 1, 1A, 2, 3, 4, 5, 6:
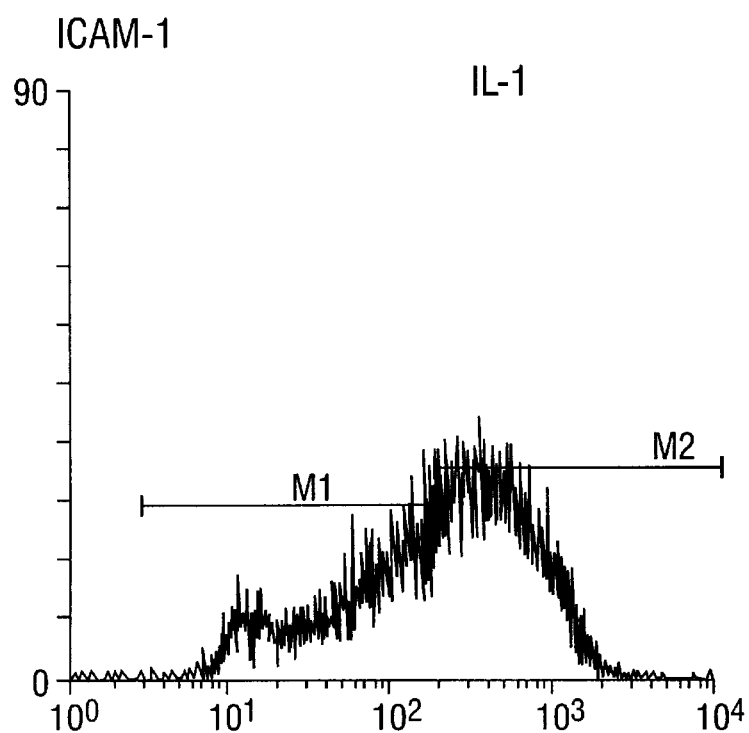
Figure 1B:
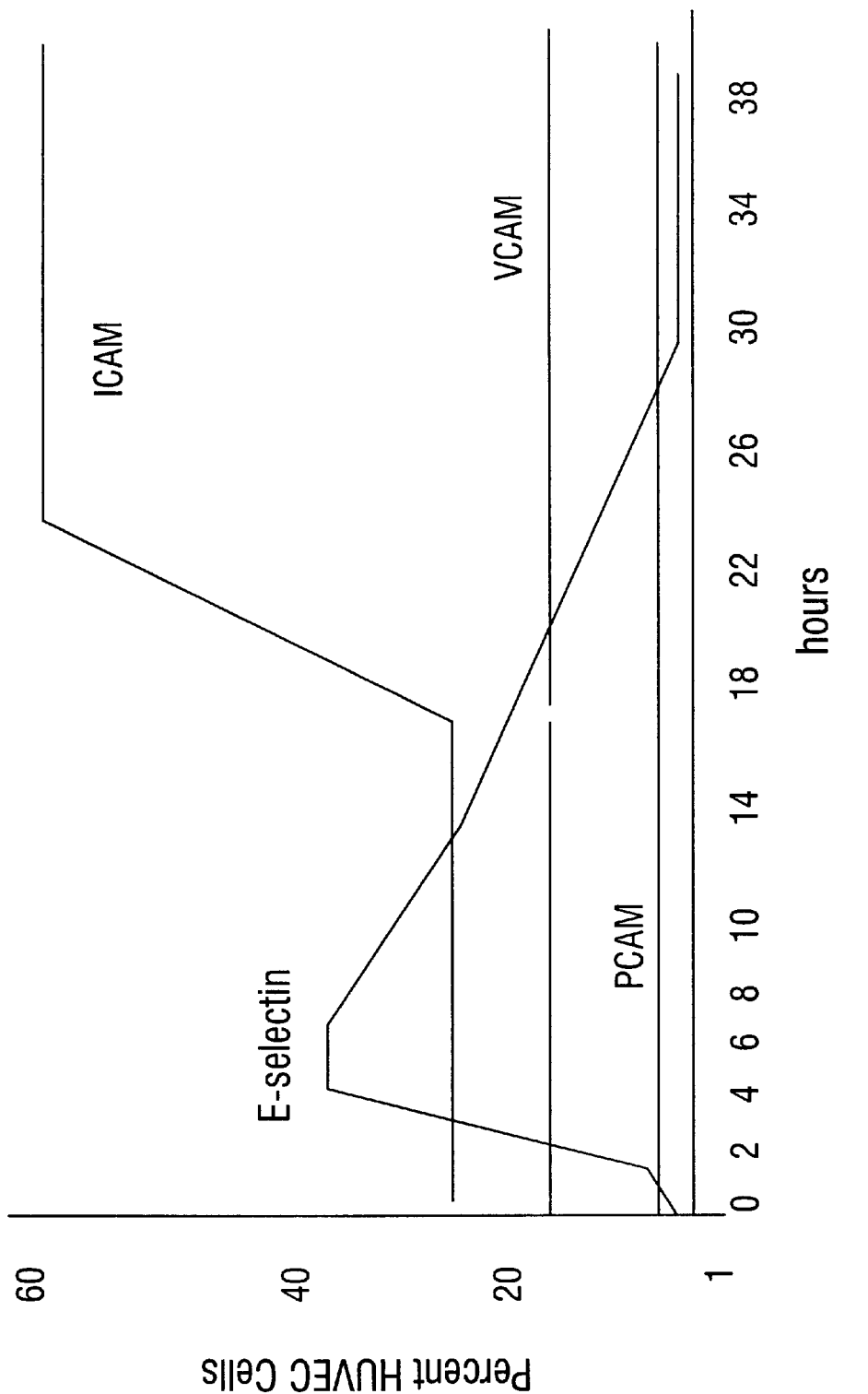
Figure 2:
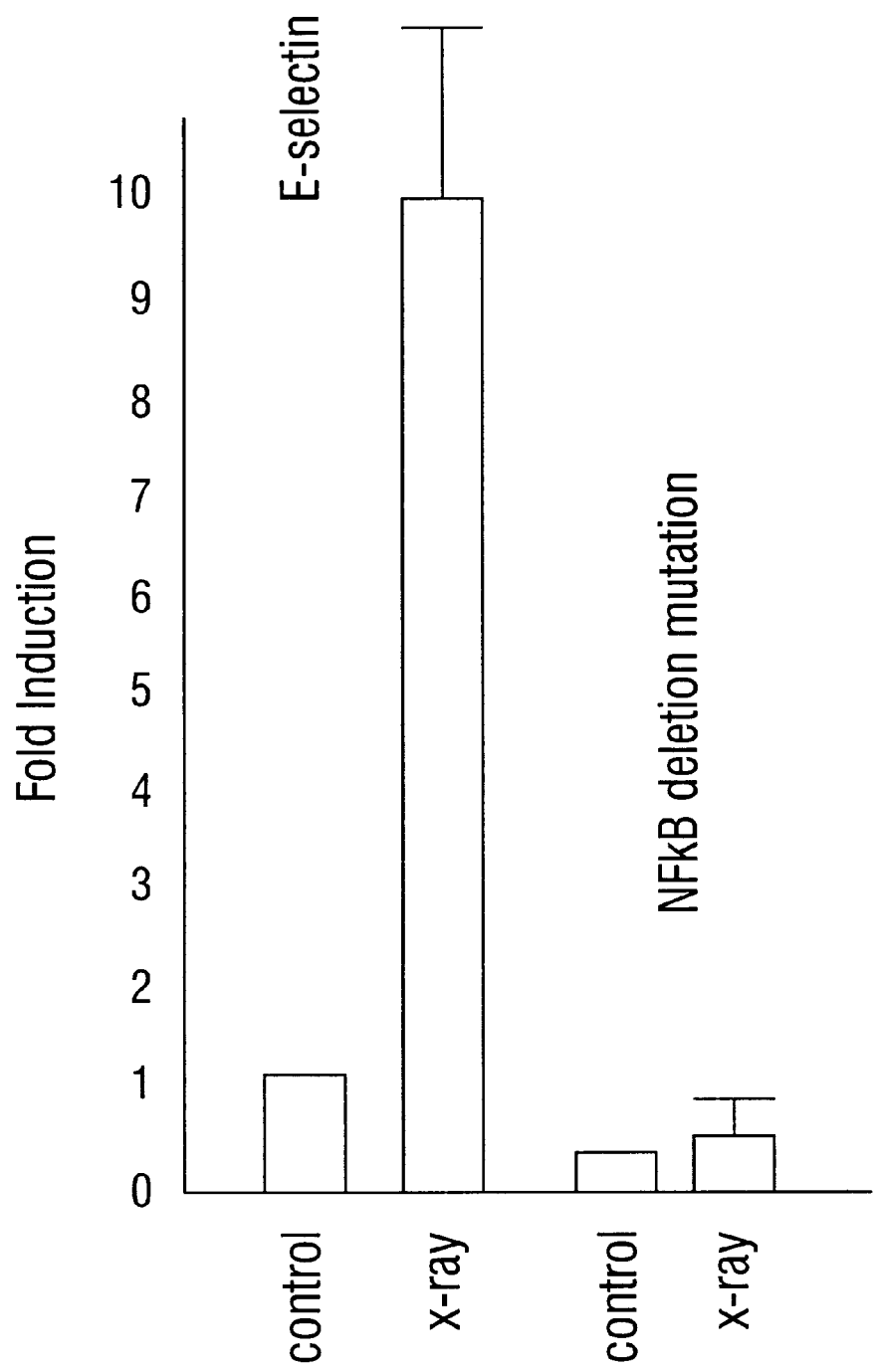
Figure 3:
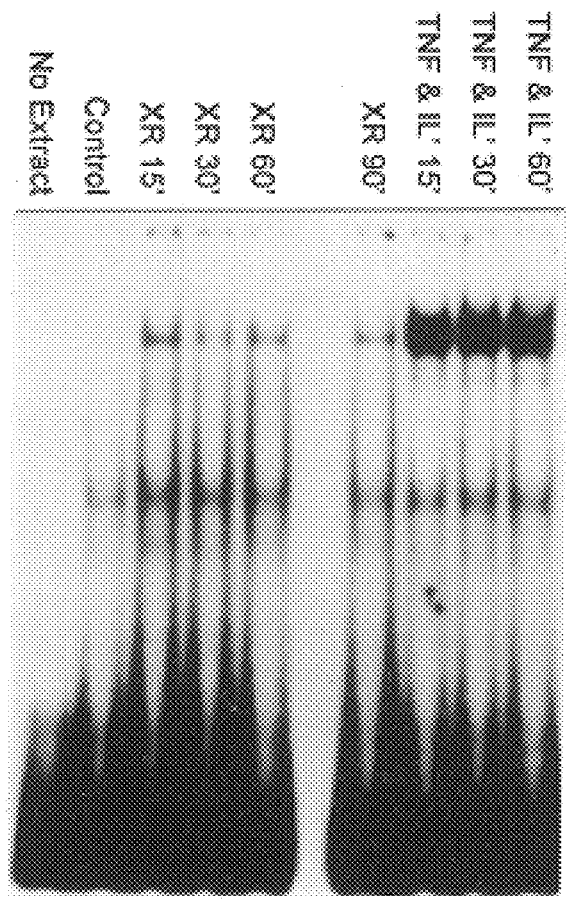
Figure 4:
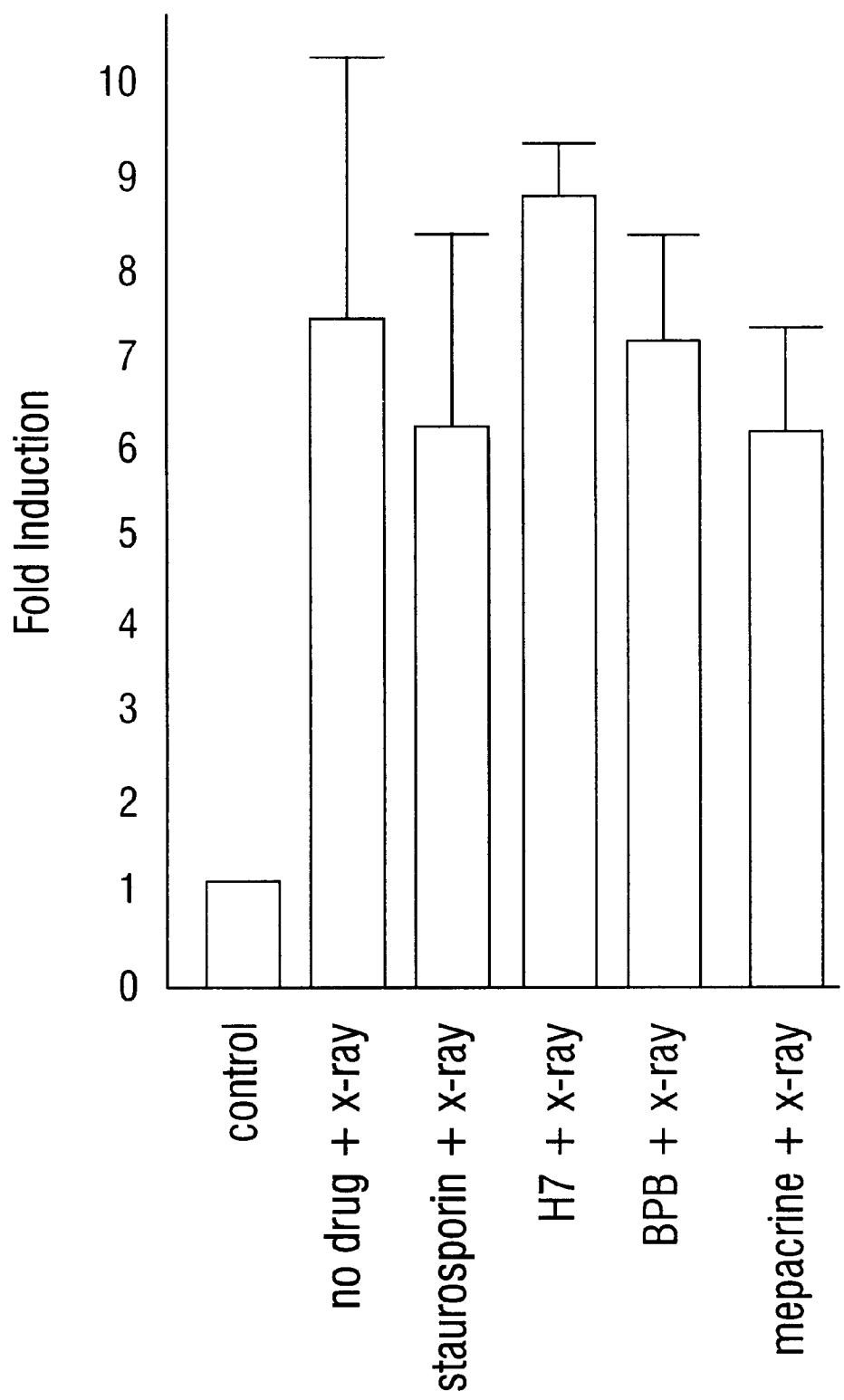
Figure 5:
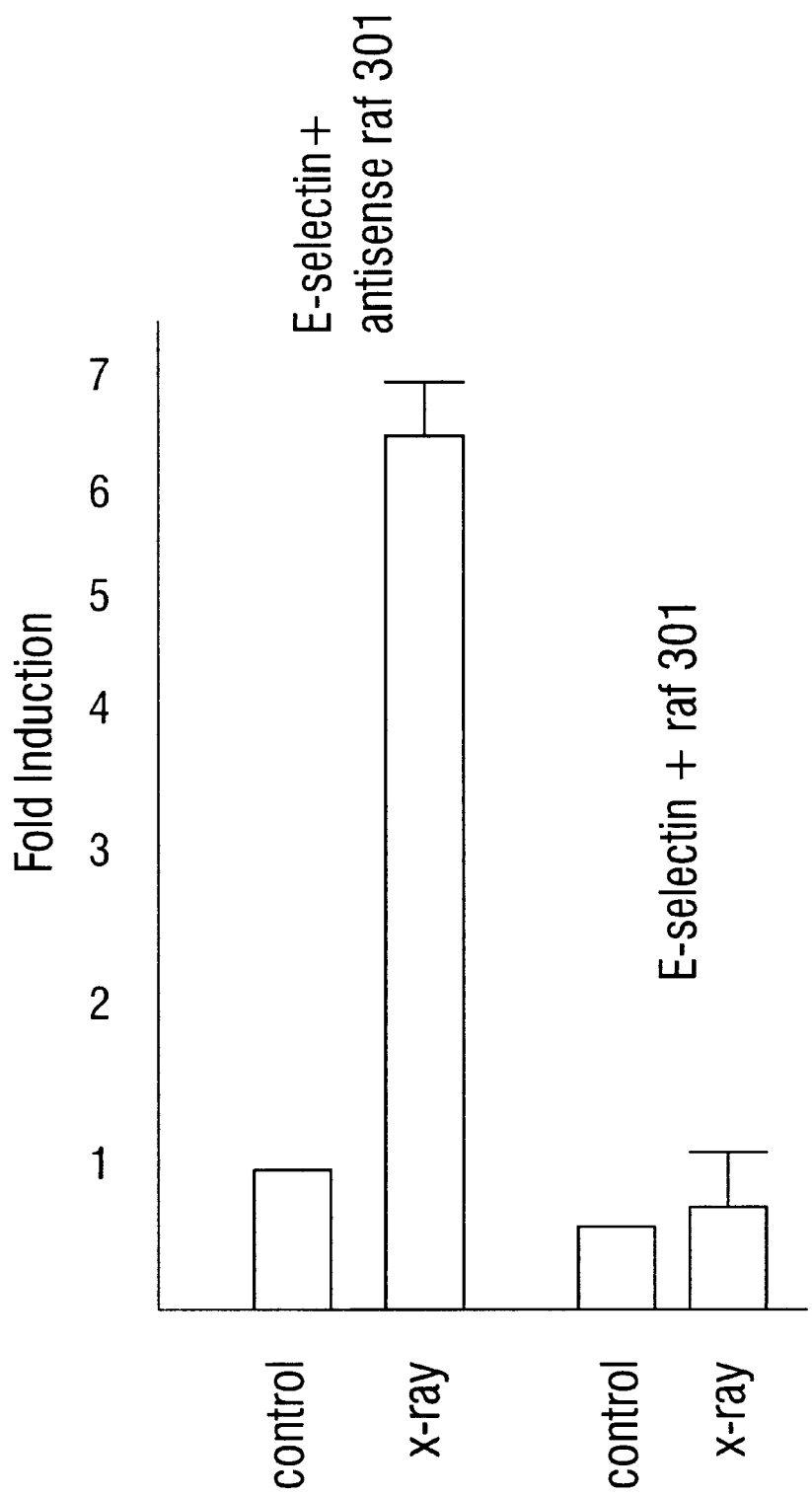

HMEC were cotransfected with pE (−578+32)-GH and Raf 301. The Raf 302 construct has the antisense orientation of the dominant negative and served as control. Raf 302 transfectants demonstrated a 4.5-fold increase in induction as compared to untreated controls (FIG. 5). Transfectants containing Raf 301 demonstrated a 50% decrease in basal expression of pE(−578) -GH and no induction after x-irradiation, whereas IL-1 and TNF induction of pE(−578) -GH remained 4.5- to 5.5-fold despite cotransfection with Raf 301. Similar results were observed in HUVEC cotransfected with pE(−578) -GH and Raf 301, indicating that x-ray-mediated E-selectin induction occurs via a signaling pathway distinct from that activated by IL-1 and TNF.

C. Discussion

Although ionizing radiation causes injury to DNA (Ward, 1988; Walker, 1985), cytoplasmic signal transduction participates in x-ray-mediated induction of some genes (Hallahan et al., 1991; hallahan et al., 1993; Uckun et al., 1992; Kharbanda et al., 1994). PKC, for example, is activated rapidly and transiently following irradiation, and PKC inhibitors prevent radiation-mediated induction of gene expression (Hallahan et al., 1991). The importance of this signal transduction pathway is that PKC-dependent signaling plays an important role in the response to both oxidative stress (Larsson and Cerutti, 1989) and the activation of NFkB (Schreck et al., 1992). Despite the strong association between radiation and PKC signaling, PKC inhibitors failed to attenuate radiation-mediated induction of E-selectin.

As Raf-1 protein kinase has been shown to participate in PKC-independent signaling (Williams and Roberts, 1994), the inventors utilized the dominant negative Raf 301 and found that it prevented transcriptional activation of the E-selectin promoter by x-rays. These data are supported by findings that Raf-1 kinase activation is associated with IkB phosphorylation, dissociation from NFkB, and subsequent kB site-dependent induction of gene expression (Li and Sedivy, 1993; Finco and Baldwin, 1993). The inventors found however, that raf301 did not prevent TNF induction of E-selectin indicating that this is not a nonspecific inhibition. Therefore, x-ray-mediated Raf kinase dependent signaling is distinct from that required for TNF and IL-1 induction of E-selectin.

EXAMPLE IV

E-selectin Induction in Endothelial Cells In Vivo

Many methods are available to induce E-selectin expression in tumor vasculature endothelial cells in vivo, as exemplified by the following.

To induce E-selectin expression in tumor vasculature endothelial cells in vivo one would, generally, expose the cells to ionizing radiation at a dose sufficient to activate the E-selectin promoter and to induce expression of the E-selectin structural gene. When using the invention to treat cancer, the tumor site itself will generally be subjected to x-ray irradiation, allowing for spatially controlled E-selectin induction, which is a particular advantage of this invention.

The inventors have shown that E-selectin expression by human endothelial cells is proportional to the dose of ionizing radiation (Example I). Effective doses were found to be between about 0.5 Gy to about 50 Gy, with E-selectin expression increasing at 4 h after exposure to 0.5 Gy, and continuing in a dose dependent manner up to 20 Gy, where a plateau was reached. Cells treated with 20 Gy or higher doses were found to have a persistent increase in E-selectin expression 24 h following irradiation.

Translating the above data into proposed clinical doses, the inventors contemplate that the tumors of cancer patients will be irradiated with between about 2 Gy up to a total dose of about 20 Gy. Daily irradiation can also be used to persistently induce E-selectin. Examples of ionizing radiation include not only x-rays, but also y-irradiation. Appropriate doses are 1–20 Gy.

E-selectin expression may also be induced in vivo in tumor vasculature endothelial cells by other means, such as, e.g., using about 150 $\mu$m $H_2O_2$ or by reperfusion with $pO_2 \geq 20$.

If, in certain clinical environments, E-selectin induction is not highly specific and E-selectin is expressed in sites of inflammation, hypoxia or reoxygenation, pre-existing E-selectin sites will be blocked with glycerrhizin prior to irradiation and addition of E-selectin-second agent conjugates or mixtures.

EXAMPLE V

Antibodies to E-selectin

Where antibodies to E-selectin are used, it is preferred to use monoclonal antibodies (MAbs), as may be obtained from a variety of commercial sources, e.g., British Biotechnology Ltd., R & D Systems, AMA Inc. and Imunotech S.A.

Antibodies to E-selectin have been described, e.g., by Mulligan et. al. (1991). These authors described CL-3 and CL-37, both of which may be used as targeting components in this invention, following radiation-induced expression of E-selectin. The methods described in the Mulligan et. al. (1991) paper may also be employed to generate new anti-E-selecting antibodies, and as a guideline to analyze the level of E-selectin expression following radiation induction.

Norton et al. (1993) used purified recombinant soluble mouse E-selectin to immunize rats to generate mAbs specific to this form of E-selectin. A panel of mAbs directed against mouse E-selectin was characterized, including five that inhibit the adhesion of HL60 cells or mouse neutrophils to COS cells expressing the mouse lectin/egf domains. These mAbs have been used to characterize the expression and function of E-selectin on cytokine stimulated murine endothelial cells.

Further suitable anti-E-selectin antibodies have been described in the literature. For example, Jutila et. al. (1992) and Steinberg et al. (1994) both described EL-246, an anti-human E-selectin antibody that recognizes and blocks E-selectin.

Groves et. al. (1991); Montefort et. al. (1992); Moughal et. al. (1992); Keelan et al. (1994a; 1994b); and Chapman et al. (1994) all reported studies using 1.2B6; and Veale et. al. (1993) used 1.3B6. ENA1 and ENA2 were described by Span et al. (1991), Hakkert et. al. (1991) and von Asmuth et. al. (1992). BBA1 was described by Zhang et al. (1994); 9H9 by Olofsson et al. (1994); CL2/6 by Abbassi et. al. (1993); and BB11 by Sporn et. al. (1993).

Still further useful anti-E-selectin antibodies have been described in Kishimoto et al. (1991); Sedmak et al. (1994); Neumann et al. (1994); Gosset et al. (1995); Span et al. (1991) and Ulich et al. (1994). Cavenagh et al. (1993) also described blocking monoclonal antibodies to E-selectin.

Should one wish to prepare a novel anti-E-selectin MAb, techniques are readily available. Means for preparing and characterizing antibodies are well known in the art (see, e.g., Antibodies: A Laboratory Manual, Cold Spring Harbor Laboratory, 1988; incorporated herein by reference). The methodological references in this area are supplemented by the specific teachings of, e.g., Mulligan et. al. (1991) and Norton et al. (1993).

The methods for generating MAbs generally begin along the same lines as those for preparing polyclonal antibodies. Briefly, a polyclonal antibody is prepared by immunizing an animal with an E-selectin immunogenic composition and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition. In this case, the immunogen will generally be a purified or partially purified E-selectin protein, polypeptide or peptide, or even a population of cells known to express E-selectin, such as HUVEC stimulated with IL-1β or irradiated HUVEC. The use of stimulated HUVECs as antigens is described by Mulligan et. al. (1991), along with appropriate selection techniques.

The immunizing composition, whether purified protein- or cell-based, is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de liovo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like. Screening hybridomas for those that react exclusively with E-selectin is also described by Mulligan et. al. (1991).

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

A molecular cloning approach could also be used to generate monoclonals. For this, combinatorial immunoglobulin phagemid libraries are prepared from RNA isolated from the spleen of the immunized animal, and phagemids expressing appropriate antibodies are selected by panning, e.g., using cells expressing E-selectin and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Functional antibody fragments, e.g., Fab', Fab, F(ab')$_2$, Fv and scFv fragments, can also be employed, so long as the antibody or fragment exhibits the desired binding specificity for E-selectin. Methods for generating active antibody fragments are well known in the art. Means for making radiolabeled Fab'-Fabs are also known (Le Duossal et. al., 1992). Methods for employing anti-E-selectin fragments, in contexts other than with radiation-induction, have also been described, which can now be utilized in the present invention.

For example, Ulich et al. (1994) used mouse F(ab')2 and F(ab') anti-E-selectin monoclonal antibodies to inhibit the emigration of neutrophils into the bronchoalveolar space following LPS injection. Silber et al. (1994) also showed that intravenous infusions of neutralizing doses of F(ab')2 fragments of murine antibodies to E-selectin during the early inductive phases of delayed hypersensitivity (DHR) resulted in the localization of the fragment to dermal endothelium at the site of DHR.

Monoclonal antibodies to human E-selectin can be labeled, e.g., using $^{125}$I, $^{131}$I, or any other desired agent, using previously described techniques. For example, using the oxidative reagent from Iodogen (Fraker and Speck, 1978) or the lactose periodase from LKB (Klein, 1989). Harrison also described astatine-211-labeling of MAbs. Mehta et al. (1990) describe methods for coupling Yttrium-90 (90Y) to diethylene triaminepenta acetic acid (DTPA) and then covalently linking this to a monoclonal antibody.

Deshpande et al. (1988) also describe an effective technique for use in labeling antibodies with copper-67. 67Cu is one of the most promising radiometals for radioimmunotherapy because of its 61.5 hr physical half-life, abundant beta particles, and gamma emissions suitable for imaging. However, 67Cu is readily transferred from the usual chelates of EDTA or DTPA to albumen. Deshpande et al. (1988) developed a new macrocycle (6-p-nitrobenzyl-TETA) to chelate copper. The bifunctional chelating agent p-bromoacetamidobenzyl-TETA was conjugated to a monoclonal antibody without significantly altering its immunoreactivity.

Many methods are also available for use in linking MAbs to anti-tumor proteins, such as, e.g., neocarzinostatin (NCS). For example, Luders et al. (1985) used the heterobifunctional reagent N-succinimidyl 3-(2-pyridyldithio)-propionate (SPDP). The conjugate retained both the reactivity of the antibody and the toxicity of the drug. Scott et al. (1987) described a method for preparing an immunotoxin-like compound composed of a monoclonal antibody linked by a disulfide bond to the ribosome-inactivating protein gelonin.

Braslawsky et al. (1990) also describe methods for chemically coupling adriamycin to monoclonal antibodies. In these studies, immunoconjugates were prepared by linking to the MAb and ADM derivative, Adriamycin 13-[3-(2-pyridyldithio)propionyl]hydrazone (ADM-HZN), which releases ADM under mild acidic conditions.

Many methods are also available for use in linking MAbs to gene segments, such as gene segments encoding anti-tumor proteins, thrombolytic agents and anticellular agents that kill or suppress the growth or cell division of disease-associated endothelial cells. Examples of effective thrombolytic agents are streptokinase and urokinase. Bode et al. (1985) described an antibody-directed urokinase that functioned as a specific fibrinolytic agent. The urokinase-MAb conjugate retained the original binding specificity of the antibody and showed 100-fold increased fibrinolysis in vitro when compared to unmodified urokinase. This technology could also be used in connection with the present invention following covalently coupling urokinase to a monoclonal antibody against E-selectin.

Collen et al. (1990) also reported on the thrombolytic and pharmacokinetic properties of a conjugate of recombinant single-chain urokinase-type plasminogen activator with a monoclonal antibody. This chemical conjugate between recombinant single-chain urokinase-type plasminogen activator (rscu-PA) and a murine monoclonal antibody was produced by cross-linking with SPDP.

In pre-clinical animal studies designed for optimization, antibodies to mouse E-selectin are contemplated to be useful. Animal models designed to allow optimization of anti-cancer strategies are routinely employed prior to translating the results to a clinical environment. Such animal models are generally held to be predictive of results in humans.

The inventors will show that ionizing radiation increases binding of E-selectin ligand-conjugated-cytotoxins in cancer xenografts in mice. Antibodies to mouse E-selectin are used here as the endothelial cells within experimental tumors will be of mouse origin. Monoclonal antibodies to murine E-selectin and Glycyrrhizin-albumin conjugates are bound to $^{131}$I and injected into the tail veins of mice 4 h after ionizing radiation exposure. $^{131}$I localization to irradiated tumors and tissues will be characterized using total body scanning as previously described (DeSombre et al., 1990; Lessem et al., 1980) and scintillation counting.

EXAMPLE VI

Targeting E-selectin with Antibody Conjugates

Primary cultures of endothelial cells were prepared from collagenase-digested human umbilical veins and maintained in M199 with 20% fetal bovine serum. HUVECs were irradiated with 10 Gy as described by Hallahan et al. (1989), or treated with otherwise identical conditions without irradiation. Biotinylated-mouse monoclonal anti-human E-selectin was added to complete medium at 4 h after irradiation with rocking at 24° C. for 30 min. HUVECs were then washed for 10 min 3 times with M199 at 24° C. Avidin bound to $^{125}$I was then added to HUVECs for 30 min. Cells were then scraped and added to scintillation fluid and $^{125}$I binding to x-ray-induced E-selection was quantified by scintillation counting. The inventors found that irradiated HUVECs had a 4-fold increase in $^{125}$I binding as compared to untreated cells.

Pre-clinically, the feasibility of using ionizing radiation to increase in vivo transfection of tumors will be proven using a predictive animal model. The inventors have already optimized the use of liposomes to transfect human tumor xenografts in nude mice. Human breast cancer xenografts in nude mice will be used to determine which model is most or best suited to study efficacy. Xenografts and analytical techniques have been described (Brunner et al., 1993; Miller et al., 1994; Weichselbaum et al., 1994; Pai et al., 1992).

Binding of E-selectin-targeted conjugates to the cells in the irradiated tumor will be compared to control unirradiated tumors in the opposite hind limb. Other controls will include tumors that are irradiated and contacted with, e.g., Lipofectin liposomes without E-selectin ligands. Furthermore, mice without tumors will receive local irradiation to lung, liver and hind limb to determine whether radiation-induction of E-selectin occurs in various tissues.

The Mulligan et. al. (1991) methodology may be used in the methods of this invention, following radiation-induction of E-selectin. These authors showed that certain MAbs blocked in vitro adherence of neutrophils to TNF alpha-treated endothelial cells and the killing of TNF alpha-treated rat endothelial cells by phorbol ester activated neutrophils. In rats treated systemically with CL-3, Mulligan et. al. (1991) reported 70% reduction in accumulation of neutrophils in glycogen-induced peritoneal exudates. When IgG immune complex deposition was induced in dermis and in lungs of rats, treatment with anti-E-selectin markedly reduced vascular injury as measured by changes in vascular permeability (leakage of 125I-albumin) and hemorrhage (extravasation of 51Cr-red blood cells).

The methodology and studies reported by Williams et. al. (1990) may also be used in conjunction with the present invention. These authors used radiolabeled antibodies to target tumor antigens. However, the strategy will be essentially the same, once E-selectin has been induced using, e.g, locally-applied radiation. The regimens described by Williams et. al. (1990) are considered to be a suitable guideline for glioma treatment. Radioiodinated anti-E-selectin antibodies ($^{125}$I-ENA1) have also been reported (von Asmuth et al., 1992), and used for internalization studies.

In a clinical setting, anti-human E-selectin is conjugated to a cytotoxic agent, such as pseudomonas exotoxin, staph endotoxin, ricin, a conventional chemotherapeutic agent, or a radioligand, such as $^{131}$I, and then given to a patient. For example, $^{131}$I bound murine monoclonal anti-human E-selectin is administered at a dose of 1 mCi 4 h after irradiation. Patients then undergo gama camera scanning to quantify the localization of $^{131}$I. This schedule of delivery is to be repeated daily to a total dose of 20 Gy from external irradiation, and the dose will be escalated by 4 Gy in cohorts of 3 patients unless a major toxicity is observed when 3 more patients will be added at that dose level.

The maximum tolerated dosage (MTD) is the dose preceding major toxicity in 2 of 6 patients. Phase II trials will follow to confirm the efficacy of x-ray localization of $^{131}$I-anti-E-selectin in locally advanced neoplasms, such as gliomas (brain tumors), and carcinomas involving the upper aerodigestive tract.

EXAMPLE VII

Oligosaccharides that Bind to E-selectin

Many oligosaccharides are known that bind to E-selectin. Still further ones can now be developed following the teaching of the present disclosure in combination with the knowledge in the art. All such oligosaccharides are contemplated for use in the present invention.

Some of the best studied E-selectin-binding oligosaccharides are the sialyl Lewis X/A compounds (Walz et. al., 1990; Phillips et. al., 1990; Berg et al., 1991). Indeed, there is general agreement that the ligands for E-selectin include sialylated, polylactosamine, oligosaccharides, with a fucose on the first {sialyl-Lewis$^x$ (sLe$^x$) epitope, Sia($\alpha$2–3)Gal ($\beta$1–4) [Fuc($\alpha$1–3)]GlcNAc—R} or second [VIM-2 epitope, Sia($\alpha$2–3)Gal($\beta$1–4)GlcNAc($\beta$1–3)Gal($\beta$1–4) [Fuc ($\alpha$1–3)]GlcNAc—R} N-acetyl-glucosamine from the non-reducing end.

Sialyl Lewis X/A compounds may either be synthesized or purchased. For example, 2–3 sLe$^x$ hexa glycolipids and 2–3 sLe$^x$ pentaglycolipids may be synthesized as described by Kameyama et al. (1991), Hasegawa et. al. (1994) and Yoshida et. al. (1993). 2–3 sLe$^x$ tetra compounds can be obtained from Glycomed (Alameda, Calif.). 2–3 sLe$^x$ hexa glycolipid is sia($\alpha$2–3)Gal($\beta$1–4) [Fuc($\alpha$1–3)]GlcNAc ($\beta$1–3)Gal($\beta$1–4)Glc-ceramide; 2–3 sLe$^x$ penta glycolipid is Sia($\alpha$2–3)Gal($\beta$1–4) [Fuc($\alpha$1–3)]GlcNAc($\beta$1–3)Gal-ceramide; 2–3 sLe$^a$ hexa is Sia($\alpha$2–3)Gal($\beta$1–3) [Fuc ($\alpha$1–4)]GlcNAc($\beta$1–3)Gal($\beta$1–4)Glc; and 2–3 sLe$^x$ tetra is Sia($\alpha$2–3)Gal($\beta$1–4) [Fuc($\alpha$1–3)]GlcNAc.

Tyrrell et al. (1991) analyzed the structural requirements for carbohydrates ligand of E-selectin and reported a detailed investigation into the minimum structural requirements for E-selectin carbohydrate recognition. Using both direct binding and inhibition studies, Tyrrell et al. (1991) demonstrated that the sialyl Lewisx tetrasaccharides Sia ($\alpha$2–3) (Gal($\beta$1–4) [Fuc($\alpha$1–3)]GlcNAc, and Sia($\alpha$2–3)Gal ($\beta$1–4) [Fuc($\alpha$1–3)]Glc are the smallest oligosaccharides recognized by the lectin. In addition, an oligosaccharide containing the sialyl Lewis$^a$ epitope was also recognized, but less avidly. A structural model of functional groups necessary for recognition by E-selectin was proposed. This model can be used to design further E-selectin-binding oligosaccharides.

The Tyrrell et al. (1991) model, together with NMR data on the conformation of oligosaccharides in solution, lead to a hypothesis for the binding face of oligosaccharides interacting with E-selectin. The Tyrrell model incorporates the following conclusions: (i) fucose and sialic acid are required for E-selectin binding; (ii) 2–6-linked sialic acid is not recognized; (iii) removal of carbons 8 and 9 on the sialic acid or substitution of an N-glycolyl for the N-acetyl of the sialic acid residue do not effect binding; (iv) removal of the N-acetyl group from the N-acetylglucosamine does not reduce binding; (v) reduction of 2–3 sLe$^x$(Glc) does not substantially reduce its inhibitory activity. The 2–3 sLe$^x$ and 2–3 sLe$^a$ oligosaccharides, in their minimum-energy conformation, present the same orientation of sialic acid, galactose, and fucose.

When linked 2–6, the sialic acid residue assumes a much different conformation in space. In the Tyrrell et al. (1991) model the glycerol side chain (carbons 7, 8, and 9) and the N-acetyl group of the sialic acid are oriented away from the recognized face of the oligosaccharide. In addition, opening the reducing terminal sugar results in three minimum-energy configurations, one of which closely matches the original configuration. The carboxyl group of the sialic acid, the 4- and 6-hydroxyls of galactose, and the 2-, 3-, and 4-hydroxyls of fucose are involved in recognition.

E-selectin-binding oligosaccharides that match the Tyrrell et al. (1991) criteria are contemplated to be particularly useful as targeting agents in the invention. The oligosaccharides described in the papers by Yuen et al. (1992; 1994), Nelson et. al. (1993), Green et al. (1992), Kojima et al. (1992), Munro et al. (1992); Mulligan et al. (1993) and Narasinga Rao et al. (1994) may also be employed as E-selectin-binding oligosaccharides, according to the following reasoning.

Yuen et al. (1992) identified another class of oligosaccharides that bind to the human E-selectin molecule using oligosaccharides on an ovarian cystadenoma glycoprotein. This was achieved by application of neoglycolipid technology to oligosaccharides released from the glycoprotein by mild alkaline $\beta$-elimination. Oligosaccharides were conjugated to lipid, resolved by thin-layer chromatography, and tested for binding by Chinese hamster ovary cells which had been transfected to express the full-length E-selectin molecule. Several components with strong E-selectin binding activity were revealed among acidic oligosaccharides. The smallest among these was identified as an equimolar mixture of the Le$^a$- and Le$^x$/SSEA-1-type fucotetrasaccharides sulfated at position 3 of outer galactose (Yuen et al., 1992).

The binding activity of this is substantially greater than those of lipid-linked Le$^a$ and Le$^x$/SSEA-1 sequences and is at least equal, if not superior, to that of the 3'-sialyl-Le$^x$/SSEA-1 glycolipid analogue. Therefore, this compound is also particularly contemplated for use in the present invention.

The 3'-sulphated Le$^a$/Le$^x$ type tetrasaccharides have also been shown to be more strongly bound to E-selectin than 3'-sialyl analogues (Green et al., 1992). A considerable binding was observed to the 3'-sulphated oligosaccharide backbone in the absence of fucose but not to a 3'-sialyl analogue or fuco-oligosaccharide analogues lacking sulphate or sialic acid. These studies highlight the relative importance of sulphate in the adhesive specificity of this protein and establish that 3'-sulphated Le$^a$/Le$^x$ tetrasaccharides are effective ligands for selectin binding. The inventors also envision using the tetrasaccharides described by Green et al. (1992) in the targeting embodiments described herein.

A further series of synthetic oligosaccharides based on sialyl Lewis$^x$ (sLe$^x$) and sialyl Lewis a (sLe$^a$) were used to study the binding interactions of selectins by Nelson et. al. (1993). These authors found that solution-phase sLe$^a$ is a more potent blocker of E-selectin than is sLe$^x$. Furthermore, addition of an aliphatic aglycone in combination with an amino substitution on the GlcNAc of sLe$^a$ resulted in a compound with 36-fold higher activity than sLe$^x$, as measured in a competitive binding assay (Nelson et. al., 1993).

More specifically, Nelson et. al. (1993) showed that the attachment of an 8-methoxycarbonyloctyl aglycone in a $\beta$ linkage to the anomeric carbon of the GlcNAc of sLe$^x$ or sLe$^a$ increased their blocking (i.e., binding) activity nearly twofold. Replacement of the 2-N-acetyl substituent of the GlcNAc by an azido or amino group resulted in substantial increases in activity, with the most potent inhibitor being amino substituted sLe$^a$, which was 36-fold more active ($IC_{50}$=21±3 $\mu$M) than the reducing tetrasaccharide sLe$^x$. Aglycone and amino substituted sLe$^a$ compounds are thus also proposed for use in E-selectin binding and targeting following site specific induction.

Yuen et al. (1994) also reported that the sulfated Le$^a$ tetra- and pentasaccharides are particularly potent E-selectin ligands. The inhibitory activity of the sulfated Le$^a$ pentasaccharide was reportedly substantially greater than that of the sialyl-Le$^x$ trisaccharide, which is currently the most widely used inhibitor of E-selectin binding: 45-, 35-, or 15-fold greater depending on whether adhesion is to sialyl-Le$^a$, sulfated Le$^a$, or sialyl-Le$^x$ pentasaccharides, respectively. These findings can be utilized in designing second generation E-selectin binding agents, as may be used in the present invention.

Mulligan et al. (1993) have described the protective effects of sialylated oligosaccharides in immune complex-induced acute lung injury. These authors showed that tetra- and pentasaccharide derivatives of sialyl Lewis$^x$ oligosaccharides derived from fucosyl transferase-expressing cells, or generated synthetically, protected against acute lung damage after deposition of immunoglobulin (Ig)G or IgA immune complexes.

In the IgG immune complex model of lung injury, which is E-selectin dependent, sialyl Lewis$^x$ oligosaccharide preparations provided dose-dependent protective effects, as assessed by changes in lung vascular permeability and hemorrhage. Protective effects were associated with diminished tissue accumulation of neutrophils in lungs. Morphological assessment revealed reduced physical contact of neutrophils with the pulmonary vascular endothelium and reduced tissue accumulation of neutrophils (Mulligan et al., 1993). These studies show that sialyl Lewis$^x$ oligosaccharides are safe for use in therapeutic embodiments.

Narasinga Rao et al. (1994) used conformational energy computations, high field NMR, and structure-function studies to define distance parameters of critical functional groups of sLe$^x$. This sLe$^x$ pharmacophore was used to search a three-dimensional data base of chemical structures. Compounds that had a similar spatial relationship of functional groups were tested as inhibitors of selectin binding. Glycyrrhizin, a triterpene glycoside, was identified and found to block selectin binding to sLe$^x$ in vitro. Using technology such as that described by Narasinga Rao et al. (1994), the inventors contemplate that other E-selectin binding agents may be identified, expanding the group of compounds available for use in this invention.

Narasinga Rao et al. (1994) also substituted different sugars for the glucuronic acids of glycyrrhizin and found the L-fucose derivative to be the most active in vitro and in vivo. A C-fucoside derivative, synthesized on a linker designed for stability and to more closely approximate the original sLe$^x$ pharmacophore, resulted in an easily synthesized, effective selectin blocker with anti-inflammatory activity.

The Narasinga Rao approach is based generally on the finding that only the charged group of sialic acid is essential to allow binding of carbohydrate epitopes to selectins (Tyrrell et al., 1991). In searching the Fine Chemicals Directory data base using MACCS three-dimensional software against a pharmacophore derived from solution conformations of sLe$^x$, compounds that matched the pharmacophore definition were identified. Such an approach may allow less expensive E-selectin-binding components to be identified.

In a first approximation, Narasinga-Rao et al. constructed a pharmacophore using the spatial dispositions of the carboxylate group of the sialic acid and the vicinal hydroxyls of fucose, which were found to be separated by 10–12 Å. In the initial two-dimensional search of ~75,000 compounds in the data base, nearly 400 compounds were identified. However, by modifying the query to more closely match the pharmacophore, the number of compounds dropped to 23 (Narasinga-Rao et al., 1994).

An examination of this list revealed that there were (i) multiple redundancy (i.e. different salt forms), (ii) organic salts, (iii) sugar-uronic acids, and (iv) modified forms of certain core structures within the list. Therefore, the list was reduced to 9 potential compounds for screening as inhibitors of selectin binding to immobilized sLe$^x$ (Narasinga-Rao et al., 1994).

In addition to glycyrrhizin and glycyrrhizic acid (NH$^+_4$), natural products from licorice, other compounds blocked selectin binding to sLe$^x$ (Narasinga-Rao et al., 1994). Of the other compounds identified in this search, the effective ones include: carminic acid, which also blocked selectin binding at concentrations comparable to those of glycyrrhizin; α-Hederin, which showed a weaker activity, inhibiting at 2–3 mM concentrations; carmine; picrocarmine; carmine ammonia; rhein-8-glucoside; kasugamycin hydrochloride; kasugamycin; meglumine diatrizoate; [ring-$^{14}$C]Chlorhexidine; trigalacturonic acid; escin; metrizoic acid (meglumine salt); and N-(α-Rhamnopyranosyloxy hydroxyphosphonyl)-Leu-Trp (sodium salt). All of these compounds have potential for use in the invention, following proper safety and efficacy testing, and are commercially available from one or more of the following vendors: Aldrich, Apin, BDH, Calbio, Fluka, ICN K&K Laboratories, Inc., Sigma, Schweitze, and TCI America.

The Narasinga-Rao et al. (1994) results indicate that 18-β-glycyrrhetinic acid, the aglycon of clycyrrhin, is relatively ineffective at blocking selectin activity (IC$_{50}$>2 mM), suggesting that the sugar residues are important for in vitro function. To further simplify the structure and to increase efficacy, glucose (Glu-O-GA), galactose (Gal-O-GAj), fucose (Fuc-O-GA), maltose (Malt-O-GA) were linked to glycyrrhetinic acid in place of the two glucuronic acid residues found on glycyrrhizin. The natural O-glycosidic linkage to the triterpene core was retained. Most of these substitutions resulted in a loss of selectin inhibition activity in vitro.

Based on these data, as well as the fact that fucose is an essential component of the native sLe$^x$ ligand for the selectins (Brandley et al., 1993), a C-fucoside of glycyrrhetinic acid (Fuc-C-GA) was synthesized (Narasinga-Rao et al., 1994). This compound was designed to incorporate a more chemically and metabolically stable carbon linkage in place of the natural O-glycosidic linkage and to more closely mimic the 10–12-Å distance between the carboxylate group and fucose in sLe$^x$. In the ELISA for selectin inhibition, Fuc-C-GA was more potent than glycyrrhizin against E-selectin and L-selectin and of equal efficacy against P-selectin. In vivo, Fuc-C-GA demonstrated greatly increased efficacy over glycyrrhizin and was equal to Fuc-O-GA.

Glycyrrhizin is used in Chinese herbal medicines as an anti-inflammatory agent (Davis and Morris, 1991) and is therefore safe for human administration. The synthetic derivatives, especially the C-fucoside of glycyrrhetinic acid, are also proposed for use in vivo. Further compounds identified by pharmacophore searches are expected to have utility in E-selectin bindding and targeting.

To label an oligosaccharide, a "bridging" molecule may be employed, e.g., albumin. For example, albumin is conjugated to glycyrrhizin and the albumin-glycoconjugate is then iodinated with $^{131}$I using previously described methods (Fraker and Speck, 1978) and lactose peroxidase from LKB (Klein, 1989). This technology can be employed with any of the E-selectin-binding oligosaccharides. Glycoconjugates of Lewis X gangliosides have also been described (Terada et.

al., 1994), and these synthetic methods may be employed in connection with the invention.

EXAMPLE VIII

Targeting Induced E-selectin with Oligosaccharide Conjugates

Following labeling of, e.g., glycyrrhizin, with a bridging molecule and ion, e.g., albumin and $^{125}$I, as described above, the binding properties of the resultant conjugate can then be analyzed. For example, $^{125}$I-glycyrrhizin-albumin conjugates are added to endothelial cells before and after ionizing radiation exposure, in an analogous manner to that described in the earlier examples for the targeting of E-selectin with antibody conjugates.

Clinically, $^{131}$I-albumin-glycoconjugate is added to HUVECs 4 h after irradiation as described above in an analogous manner to that in the earlier examples. The $^{131}$I-albumin-glycoconjugate binding to x-ray-induced E-selectin is then quantified by scintillation counting. Efficacy is determined by colony form assay as described in Hallahan et al.( 1989). Tumor regression is analyzed as described in Weichselbaum et al. (1994).

The doses of radiolabeled glycyrrhizin or glycyrrhizin-selected agent conjugates for use in human diagnosis or treatment protocols are contemplated to be within the ramge of the doses previously employed with glycyrrhizin in non-radiation methods. For example, Soma et. al. (1994) described the effect of glycyrrhizin on cortisol metabolism, in which 225 mg/day of glycyrrhizin was given for seven consecutive days.

Okunu et. al. (1994) gave large doses of glycyrrhizin to patients with hepatitis C. The doses described by Okunu et. al. (1994) could also be employed in the invention. Numazaki et. al. (1994) gave glycyrrhizin to children with liver dysfunction associated with CMV infection. Specifically, 0.2% glycyrrhizin was dissolved in saline to 2 mg/ml, supplemented with glycine and cystein and administered intravenously at 50 ml/day for more than one week. This is also contemplated effective dosage range for use in this invention.

Akao et. al. (1994) gave 100 mk/kg glycyrrhizin orally to rats, when it was found that glycyrrhizin itself is poorly absorbed from the gut. This should be taken into account in optimizing the appropriate doses of glycyrrhizin and glycyrrhizin-containing formulations. Tsai et. al. (1992) also gave glycyrrhizin at doses of 100 mk/kg. However, it is important to note that Krahenbuhl et. al. (1994) gave doses of 18β-glycyrrhetic acid, a major metabolite of glycyrrhizin, to healthy human volunteers in up to doses or 1500 mg orally.

EXAMPLE IX

E-selectin-Binding Polysaccharides and Glycoproteins

Human protein C also inhibits selectin-mediated cell adhesion. The human anticoagulant factor, Protein C, is a unique fucosylated plasma glycoprotein that has reported anti-ischemic and anti-inflammatory properties. It has been reported that both human plasma-derived and human cell-produced recombinant Protein C inhibit E-selectin-mediated cell adhesion (Grinnell et. al., 1994). This effect was reportedly not mediated through the serine protease activity of Protein C, but through its carbohydrates. Using oligosaccharides isolated from human cell-produced Protein C, Grinnell et. al. (1994) defined a polylactosamine structural determinant that inhibits adhesion. This uncharged determinant appears to be a more potent ligand for E-selectin than the sialylated Lewis X antigen (Grinnell et. al., 1994), and can therefore also be used in the present invention.

A 150-kD glycoprotein ligand for E-selectin has also been found on mouse myeloid cells (Lenter et. al., 1994). In addition, glycoproteins of 230 kD and 130 were identified on mature mouse neutrophils that also bound both to E-selectin in a Ca(2+) dependent fashion (Lenter et. al., 1994), although the signals detected for these ligands were 15–20-fold weaker than those for the monospecific ligands. All of these glycoproteins are contemplated for use as E-selectin binding ligands, as are polysaccharides, such as polylactosamine.

EXAMPLE X

Liposomes as Agents for E-selectin Delivery

Oligosaccharides, polysaccharides or glycolipids may be used alone as the targeting component of a drug delivery agent, or may be formulated into liposomes, or attached to a liposome, resulting in a liposomal targeting and delivery agent.

Glycolipid liposomes containing marker genes (e.g., LacZ) were used to transfect endothelial cells before and after ionizing radiation exposure in vitro. Primary cultures of endothelial cells were prepared from collagenase-digested human umbilical veins and maintained M199 with 20% fetal bovine serum. Primary culture HUVEC cells were expanded from single umbilical veins irradiated followed by fixation and incubation with antibodies to adhesion molecules (Examples I and II). Endothelial cells from human dermis immortalized with SV40 (HMEC) (Ades et al., 1992) were maintained as described in Example I. Endothelial cells were irradiated with 10 Gy and incubated with antibody at 2 h intervals.

The inventors have optimized the transfection of marker genes into both HUVEC and HMEC human endothelial cells using DOTMA/DOPE liposomes (Lipofectin reagent, BRL GIBCO). Following the present discovery regarding E-selectin, glycolipids that bind to E-selectin are formulated into liposomes to improve the transfection efficiency following low dose irradiation of the target cells.

HUVEC and HMEC cells are irradiated with 50, 100, or 200 cGy. Four h following irradiation, cells are transfected with LacZ expression vectors using, e.g., a sialyl Lewis X-DOTMA conjugate or a anti-E-selectin-DOTMA conjugate. The optimal time for exposure of HUVEC and HMEC cells to Lipofectin is about 6 h. Therefore, following irradiation, cells are exposed to sialyl Lewis X-DOTMA conjugate for 2, 4, 6, or 8 h to determine which time period is optimal for reducing the transfection time. Controls include irradiated cells transfected with Lipofectin and unirradiated cells transfected with sialyl Lewis X-DOTMA conjugate. LacZ encodes β-galactosidase and this enzyme is quantified as previously described by Hallahan et al. (1992).

Naturally, in addition to oligosaccharides, polysaccharides and glycolipids, any other E-selectin targeting agent could be formulated into a liposome preparation and used for delivery and targeting. The liposomes may contain any selected agent, whether in the form of a gene therapy agent, a protein, toxin, radionuclide and the like.

Liposome formulations particularly contemplated for use include DOTMA, DOTMA/DOPE and DORIE. However, virtually any liposome that binds to E-selectin may be employed. Liposomes and nanoparticles are known to be safe for human administration. For example, they have been used in the targeted antibiotic therapy of intracellular bacterial infections and diseases as they can generally entrap, and then liberate antibiotics such as ampicillin in a stable and reproducible way (Henry-Michelland et al., 1987).

Further liposome formulations contemplated for use in the present invention include cationic liposomes. Trubetskoy et al. (1992) showed that cationic liposomes enhanced targeted delivery and expression of exogenous DNA mediated by N-terminal modified poly(L-lysine)-antibody conjugate in mouse lung endothelial cells. DNA:antibody conjugates and cationic liposomes form a ternary electrostatic complex which preserves the ability to bind specifically to the target cells. The addition of liposomes has been reported to enhance the specific transfection efficiency of antibody-polylysine/DNA binary complex by 10 to 20-fold in mouse lung endothelial cells in culture (Trubetskoy et al., 1992). The utilization of these types of methods, following E-selectin radio-induction as provided by this invention, is contemplated to be particularly useful.

Liposomes may also be used in conjunction with anti-E-selectin antibodies, as described by Klibanov et al. (1991). Such liposomes coupled to monoclonal antibodies, termed "immunoliposomes", have been reported to show specific localization in vivo Klibanov et al. (1991). This will provide an added advantage when used with the present invention, in which specific E-selectin would have previously been induced. Liposomes made by conjugating a targeting antibody directly to the liposome surface were also reported to be efficiently internalized and retained in studies by Matthay et al. (1989).

To avoid side effects due to intracellular polymeric overloading, ultrafine particles (sized around 0.1 µm) may be designed using polymers able to be degraded in vivo. Biodegradable polyalkyl-cyanoacrylate nanoparticles that meet these requirements may be used. They are easily made, as described by Couvreur et al. (1984, U.S. Pat. No. 4,489, 555; 1988). More recently, liposomes were developed with improved serum stability and circulation half-times (Gabizon & Papahadjopoulos, 1988; Allen & Choun, 1987).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUvs) with diameters in the range of 200 to 500 Å, containing an aqueous solution in the core.

Liposomes bear many resemblances to cellular membranes and are contemplated for use in connection with the present invention as carriers for the second agents and/or genes. They are widely suitable as both water- and lipid-soluble substances can be entrapped, i.e., in the aqueous spaces and within the bilayer itself, respectively. It is possible that drug-bearing and gene-bearing liposomes may even be employed together for site-specific delivery of active agents to E-selectin expressing cells.

Liposomes have been used to transfect syngeneic tumors cells in vivo following irradiation of human tumor xenografts and syngeneic tumor models, so their safety has been established. Pro4L murine fibrosarcoma is a syngeneic tumor model that has been used. Tumor cells are injected subcutaneously into the hind limb of mice. Tumors are grown to 160 mm$^3$. Liposomes containing pE-sel-TNF are injected directly into tumors or administered systemically.

Tumors are irradiated (10 Gy) 24 h after liposome injection. TNF is quantified from excised tumors as described by Weichselbaum et al. (1994), and tumor control is quantified as described by Weichselbaum et al. (1994).

The above model can be easily adapted for use in the present invention. Liposomes are used to transfect tumor vasculature endothelial cells in vivo, following initial irradiation of the tumor to induce E-selectin. After irradiation and E-selectin induction, liposomes are injected directly into tumors, directed to the tumor site using a catheter, or administered to the animal systemically. The use of iridium wire in blood vessels to control vascular gene therapy in a site directed manner is also contemplated. Tumors are then irradiated again (10 Gy) 24 h after liposome injection and TNF and tumor regression is quantified.

The use of liposomes in gene transfer has been established to be safe. For example, Caplen et. al. (1995) used liposomes to transfer the CFTR gene to the nasal epithelium to patients with cystic fibrosis. If delivery to the nasal epithelium was specifically desired, the techniques of Caplen et. al. (1995) could be followed, after local irradiation to induce E-selectin.

The use of antitumor drugs housed within liposomes conjugated with anti-tumor antibodies has also been described (Konno et al., 1987; Betageri et al., 1993). These methods for the immunospecific delivery of drugs and other materials to antigenic target cells can be adapted for use in this invention.

EXAMPLE XI

Viruses that Bind to E-selectin

Binding of gene therapy viral vectors to endothelial cells is also increased by x-irradiation, in part, by way of E-selectin induction. This is shown by adding replication deficient Adenovirus type 5 (McGrory et al., 1988) containing the LacZ reporter gene (AD5-LacZ) to HUVEC's before and after irradiation.

Cells were grown to 90% confluence and irradiated with 10 Gy, as described in the earlier examples and in Hallahan et al. (1989), or treated with otherwise identical conditions without irradiation. $10^6$ to $110^7$ viral particles were added to cultures in 1 ml of medium for 2 h with gentle rocking at $pCO_2$ 6.0 and 35° C. Ad5-LacZ was then removed and cell cultures were washed and complete medium was added. LacZ transfection was quantified by the β-galactosidase assay as described in Hallahan et al. (1992). It was found that irradiated HUVEC had a 2.5 fold increase in LacZ expression as compared to unirradiated controls.

Following approval by the FDA, cancer patients will be treated with the following protocol: Tumors will be irradiated with about 2 Gy and then subjected to Ad5 (Egr-TNF) (McGrory et al., 1988).

Ad5 (Egr-TNF) will be administered at a dose of about $10^8$ about 4 h after irradiation. Patients will then undergo tumor biopsy to quantify the localization of TNF, as determined by ELISA assay using the method described by Weichselbaum et al. (1994). This schedule of delivery will be repeated daily to a total dose of 20 Gy from external irradiation and the dose will be escalated by 4 Gy in cohorts of 3 patients, unless a major toxicity is observed when 3 more patients will be added at that dose level. The maximum tolerated dosage (MTD) will be determined as the dose preceding major toxicity in 2 of 6 patients.

Once the MTD is found, a phase II trial will confirm the efficacy of x-ray localization of viral vector gene therapy in locally advanced neoplasms, such as, e.g., gliomas (brain tumors), and carcinomas involving the upper aerodigestive tract.

EXAMPLE XII

Cells that Bind to E-selectin

Targeting leukocytes containing therapeutic genes, or other selected agents, to tumor vasculature is another element of this invention.

Both neutrophils and eosinophils have been shown to bind to the inducible endothelial cell adhesion molecule E-selectin. Counter ligands on eosinophils for E-selectin have been identified as sialyl dimeric le(x) compounds (Bochner et. al., 1994). It has also been demonstrated that human CD56+CD16+/CD3-NK cells adhere to the E-selectin expressed by stimulated HUVEC in a sialidase- and Ca(2+)-dependent manner (Pinola et. al., 1994).

Norton et al. (1993) and Lo et al. (1994) also showed that human neutrophils bind to E-selectin. Wakita et al. (1994) demonstrated that E-selectin is the critical adhesion molecule for trafficking of memory T cells into certain skin lesions. Olofsson et al. (1994) also showed that E-selectin mediates leukocyte rolling in interleukin-1-treated rabbit mesentery venules.

A subset of human helper memory T cells is known to adhere to E-selectin expressed on cytokine-activated endothelial cells. A distinct type of sialyl Lewis X antigen, defined by a novel monoclonal antibody, has been shown to be selectively expressed on helper memory T cells (Ohmori et. al., 1993). Of the various molecular species of sialyl Lex antigens present on carbohydrate side chains of cellular glycoproteins, it has been reported that helper memory T cells express a distinct type of sialyl Lex antigen. Cultured ATL cells expressing the 2F3-defined antigen showed a clear E-selectin-dependent adhesion to cytokine-activated endothelial cells (Ohmori et. al., 1993).

HL525 cells were transfected with the radiation inducible genetic construct pEgr-TNF as described by Weichselbaum et al. (1994). HL525 cells, 5×10$^5$ cells/ml, were plated [medium 4-(2-hydroxyethyl)-1-piperazineethane sulfonic acid-HEPES-buffered RPMI 1640, 20% fetal bovine serum, 1 mM sodium pyruvate, 100 μM minimal essential medium nonessential amino acids, 100 units/ml penicillin, and 100 μg/ml streptomycin] 24 h prior to transfection.

On the day of transfection, the HL525 cells were resuspended at a concentration of 2×10$^7$ cells/ml in cold RPMI 1640 buffered with HEPES, and 0.5 ml was aliquoted into each electroporation curvet. The following DNAs were added to the cells in the cuvet: 10 μg XhoI linearized pEgr-TNF DNA, 1.5 μg pCB6+DNA (a neo resistance plasmid) (25); and 1.0 μg cytomegalovirus β-galactosidase DNA. The solution was gently mixed and allowed to incubate at room temperature for 5 min. The cells were transfected by electroporation at 350 V/960 μF. The cuvets were then allowed to stand for 15 min after which the cells were cultured in complete medium for 48 h. The cells were subcloned in G418 (1200 μg/ml) by plating 0.5 cell well in 96-well plates. These subclones were grown and maintained in G418 and tested for TNF induction. The subclone HL525 Egr-TNF clone 2 gave the greatest X-ray induction of TNF and is the clone used in these studies.

The resulting HL525 (Egr-TNF) clones were added to HUVECs in an analogous manner to that described by Jones et al. (1995). HL525 (Egr-TNF) cells were added to HUVECs after exposure to 10 Gy, or cells treated with otherwise identical conditions without irradiation. Cultures were washed to remove nonadherent clones. The Egr-TNF was activated by irradiation and TNF was released into the medium. TNF was quantified by ELISA assay as described by Weichselbaum et al. (1994). It was found that TNF levels were increased in cultures in which HUVECs were first irradiated to activate cell adhesion molecules as compared to unirradiated cells.

As shown by Weichselbaum et al. (1994), female nude mice bearing SQ-20B xenografts (75–320-mm$^3$ volume) were given injections of HL525.Egr-TNF clone 2 cells (5×106 cells in 100 μl PBS) immediately prior to a single dose of 20 Gy. Mice were shielded with lead so that only tumors were irradiated. Nonirradiated tumors served as controls. Animals treated with radiation and clone 2 demonstrated an increase in tumor cures compared with animals treated with radiation alone or unirradiated animals given injections of clone 2 alone. No increase in local or systemic toxicity was observed in the combined treatment group.

There were no observable differences in local skin desquamation or soft tissue necrosis between animals treated with radiation alone and the combination of radiation and the TNF-α inducible clone 2. Pathological examination of representative normal tissue sections revealed no differences in fibrosis between the radiation and radiation, TNF groups. There were no differences in weights between animals treated with radiation alone [25.33±0.408 (SD) g] and radiation/TNF 925.27±0.724 g). This result is consistent with the findings that no TNF was detectable in the serum of the animals treated with radiation and clone 2 and that no systemic TNF-α toxicity was observed.

These studies of Weichselbaum et al. (1994) can be adapted for use in the present invention by irradiating the tumor site first to induce E-selectin expression. This new E-selectin-mediated therapy is thus contemplated to enhance tumor cures without increasing normal tissue toxicity, particularly when used with gene therapy.

A version of this technology is contemplated for use in cancer patients after approval by the FDA. Tumor infiltrating lymphocytes (TIL) are obtained from the vascularized tumor site of an animal, e.g., as described by Hwu et al. (1993). They are then transfected with the murine retrovirus containing radiation inducible Egr-TNF construct. Retrovirus vectors are prepared using previously well described techniques (e.g., Treisman et al., 1994, Hwu et al., 1993).

Transfected TIL cells have been used to treat cancer (Hwu et al., 1993). These authors showed that TNF is effective in causing the regression of selected murine tumors when administered at high concentrations. Therapeutic levels in humans cannot be obtained systemically, however, because of dose-limiting toxicity. The development of immunotherapy with IL-2 and tumor-infiltrating lymphocytes (TIL), which can accumulate at tumor sites in some patients, and of efficient retroviral techniques for gene transfer into eukaryotic cells has allowed new therapeutic approaches using TNF.

Hwu et al. (1993) retrovirally transduced human TIL with the gene for TNF in an attempt to deliver high concentrations of TNF to the tumor site without dose-limiting systemic toxicity. Successful gene insertion was confirmed and transduced selected TIL cultures produced greater amounts of TNF, compared with nontransduced controls. In an attempt to increase TNF production, TIL were transduced with a mutated form of TNF containing the IFN-γ signal peptide in place of the transmembranous region, to enhance secretion into the endoplasmic reticulum.

By using the new vector, TNF production increased by an average of fivefold. These studies of Hwu et al. (1993) demonstrate that TIL can be genetically modified to express and secrete a protein for use in targeted cancer therapy.

More specifically, Hwu et al. (1993) used the following methods. TIL were derived from enzymatically digested tumor biopsies as well known in the art. Briefly, melanoma tumor biopsies were digested overnight with collagenase type IV (1 µg/ml), hyaluronidase (0.1 µg/ml), and DNase (30 U/ml) (Sigma Chemical Co., St. Louis, Mo.). After digestion, the single-cell suspensions were passed through a sterile wire screen grid and subjected to Ficoll-Hypaque separation to remove dead cells and RBC.

TIL cell cultures were established at $5.0 \times 10^5$ cells/ml in 24-well sterile tissue culture plates, in medium consisting of RPMI 1640 supplemented with 10% human A serum (Bio-Whitaker, Walkersville, Md.). This medium was mixed 1:1 (v/v) with AIM V serum-free medium (GIBCO, Grand Island, N.Y.) and was further supplemented with gentamicin sulfate (10 µg/ml), penicillin G sodium (10,000 U/ml), glutamine (200 mM) (all from GIBCO), 7200 IU/ml IL-2 (Cetus, Emeryville, Calif.), and 10% (v/v) lymphokine-activated killer cell-conditioned supernatant.

Because TIL can double every 2 to 4 days, TIL densities were maintained at $5.0 \times 10^5$ by splitting cultures every 3 to 5 days with fresh medium containing IL-2 and passaging cells to larger cell culture plates (six-well) when required. When TIL reached greater than $2 \times 10^8$ in number, they were cultured i AIM V serum-free medium alone containing 6000 IU/ml IL-2. The culture vessels used for large-scale expansion were gas-permeable PL732 3-liter plastic bags (Fenwal, Deerfield, Ill.).

Melanoma tumor cell lines were derived from the same enzymatically digested melanoma tumor biopsies as were used to generate TIL. Tumor cell cultures were established in 24-well sterile tissue culture plates in RPMI 1640 plus 10% heat-inactivated FCS. When colonies of melanoma tumor cells became evident, they were allowed to grow to confluence before passage to larger culture vessels. The presence of melanoma tumor cells was verified by FACS analysis by using FITC-conjugated anti-GD3 mAb (Mel-1) obtained from Signet Laboratories (Boston, Mass.).

The solely secretable TNF vector was constructed by replacing the 5' transmembrane portion of the TNF cDNA with the signal peptide from IFN-γ, thereby leaving only the sequences coding for the 17-kDa secreted TNF peptide. The 17-kDa solely secretable TNF retroviral vector was received from the Chiron Corp.

TIL were pelleted and resuspended at $1 \times 10^6$ cells/ml in AIM V with 6000 IU/ml IL-2, in a 1-ml volume, in 24-well plates (Costar, Cambridge, Mass.). Retroviral supernatants were supplemented with protamine sulfate to a final concentration of 5 µg/ml (Eli Lilly & Co., Indianapolis, Ind.) and were then added in a 1-ml volume/well. Twenty-four hours later, 1 ml was aspirated from each well and replaced with 1 ml of freshly thawed retroviral supernatant, again supplemented with fresh IL-2 and protamine. Forty-eight to 72 h after transduction, TIL were aliquoted into several groups, and each was partially selected for 5 days by using a different concentration (0, 0.1, 0.3, or 0.5 mg/ml) of the neomycin analogue Geneticin (G418; GIBCO).

A melanoma tumor line (888 MEL) was transduced with the TNF gene in a similar manner, but in the absence of IL-2, and was fully selected by continuous growth in the presence of 0.6 mg/ml G418. This fully selected, transduced, melanoma line (MEL-TNF) was used throughout the study as a positive control for successful gene transfer and expression. MEL-TNF cells were estimated to contain a single copy of the TNF vector, based on comparison of signal intensity on Southern blots with that of the cloned retroviral producer cells. The producer cells were previously shown to contain only a single copy of the TNF vector by demonstration of a single band on Southern blot after restriction digestion of a unique BamHI site within the vector.

The methods described by Hwu et al. (1993) can be adapted for use in the present invention with the added advantage that by irradiating the tumor site first, E-selectin expression will be induced, allowing for enhanced targeting. Transfected TIL cells are injected as described by Hwu et al. (1993) 4 h after induction of E-selectin by irradiation of tumors. Lymphocytes will bind to E-selectin, as previously described (Jones et al., 1995).

After TILs have bound to irradiated tumors (1 h after infusion), tumors will again be irradiated to activate the radiation inducible Egr-TNF. The resulting TNF produced by irradiated TILs will induce E-selectin further within this confined volume and additional TILs will injected and again activated with irradiation. The techniques described by Treisman et al. (1994) regarding trans retinoic acid (RA)-enhanced gene expression in TILs may also be employed to supplement the teachings of Hwu et al. (1993).

Following isolation from the animal to be treated, TILs may also be transfected with the fucosyltransferase (ELFT) gene before re-administration. The mammalian cDNA encoding alpha (1,3)-fucosyltransferase is widely available, as described by Goelz et al. (1990); Lowe et al. (1990, 1991); and Kumar et al. (1991). Transfection into the appropriate cell types results in cells that express SLex and bind to E-selectin (Goelz et. al., 1994).

EXAMPLE XIII

Cellular Ligands that Bind to E-selectin

Distinct cell surface ligands mediate T lymphocyte attachment and rolling on E selectin under physiological flow (Alon et. al., 1994). Such antigens can be used in conjunction with the present invention.

The HECA-452 antigen is a homing receptor for lymphocyte migration into skin. HECA-452 was later identified as a group of related sugar moieties that bind to E-selectin. Direct evidence has been reported to show that the antigen recognized by HECA-452 is involved in the adhesion of leucocytes to endothelial cells, and that this antigenic epitope is different from that reactive to the sialylated Lewis X antigen (De Boer et. al., 1994). The HECA-452 antigen can also be used in conjunction with the present invention.

The ligand L-CanAg (light cancer antigen), secreted by a colon carcinoma cell line COLO 205, may also be used in certain selected binding embodiments (Zhang et al., 1994), particularly those in vitro assays, such as conducted on biopsy material.

EXAMPLE XIV

Vectors and Gene Therapy Following E-selectin Induction

The field of gene transfer into vascular cells is emerging as a new approach for studying the pathophysiology of vascular disease and for developing potential new genetic treatments for these disorders (Nabel et. al., 1994). E-selectin-mediated control of vascular gene therapy forms another aspect of the present invention. The text and figures of Nabel et. al. (1994) and Gutierrez et al. (1992) are incorporated herein by reference for the purposes of even further supplementing the present disclosure in terms of describing gene transfer strategies and vectors, genes and antisense oligonucleotides, drugs, viral vectors, liposomes, animal models of vascular gene transfer, normal tissue protection, and the like.

Recombinant vectors capable of expressing a protein in vascular endothelial cells will be targeted to such cells using an E-selectin binding moiety. The vectors may have an ionizing radiation-inducible promoter that directs the expression of the protein, in which case, a subsequent round of irradiation will induce expression of the encoded protein in the cells. Effective ionizing radiation-inducible promoters include the CArG domain of the Egr-1 promoter, the fos promoter, the c-jun promoter and the TNF-α promoter.

Recombinant vectors could also employ vascular endothelial cell-specific promoters to direct gene expression. The use of the E-selectin promoter to control gene therapy with radiation is particularly contemplated. The E-selectin gene promoter has been linked to TNF cDNA using a blunt end ligation of TNF cDNA into the plasmid pE-sel-hGH (Collins et al., 1991; Read et al., 1994). The resulting plasmid pE-sel-TNF was contransfected with pCMV-LacZ (β-galactosidase) into human endothelial cells (HUVEC and HMEC). Cells were then irradiated with 5 Gy. TNF and β-galactosidase expression and cell killing was observed. Thus, pE-sel-TNF combined with radiation is extremely cytotoxic to endothelial cells.

An E-selectin promoter-structural gene construct, as exemplified by E-selectin TNF, may be delivered to a target endothelial cell in vivo using virtually any E-selectin-binding agent. For example, linking DNA to antibodies has been described. In certain preferred embodiments, cells, viruses or liposomes will be used to house E-selectin promoter-structural gene constructs and to deliver them to the tumor vasculature cells in vivo, following irradiation of the tumor site. Antibody-gene constructs can also be employed, as described hereinabove. Destruction of the endothelium is a primary means of tumor cure by TNF. The tumor vasculature is obliterated resulting in hemorrhagic necrosis. Therefore, pE-sel-TNF combined with radiation is used in vivo in vascular tumors to achieve tumor control.

The vectors will generally direct the expression of an anticellular agent capable of killing or suppressing the growth or cell division of tumor-associated endothelial cells. One group of such anticellular agents are the tumor suppressor proteins, such as p53, p16 (Kamb et. al., 1994), proteins produced in response to p53, the retinoblastoma gene product (Rb), the Wilms' tumor gene product (WT1), and certain cyclins (Marx, 1994). In addition, further tumor suppressors include APC, DCC, NF-1, NF-2, MEN-I, MEN-II, BRCA1, VHL, FCC and MCC.

The protein p53, a 53 kD nuclear phosphoprotein that controls cell proliferation, is one example of a tumor suppressor. The p53 protein is highly conserved through evolution and is expressed in most normal tissues. Point mutations in the p53 gene and allele loss on chromosome 17p, where the p53 gene is located, are among the most frequent alterations identified in human malignancies. Even single base substitution in p53 can result in p53 proteins with altered growth regulatory properties, which leads to cancer.

The p53 gene has been found to be the most frequently mutated gene in common human cancers (Hollstein et al., 1991; Weinberg, 1991), and is particularly associated with those cancers linked to cigarette smoke (Hollstein et al., 1991). The over-expression of mutated p53 in breast tumors has also been documented (Casey et al., 1991). Transfection of wild-type p53 into certain types of breast and lung cancer cells can restore growth suppression control in cell lines.

Although the present invention concerns targeting to tumor vasculature endothelial cells, the delivery of a tumor suppressor gene, such as p53, to the cancer environment using this invention is contemplated to be useful. Supplying the normal tumor suppressor proteins may serve to suppress the growth of the endothelial cells, and may even act on certain tumor cells themselves, following uptake into tumor cells in the vicinity of the blood vessels. In a similar manner, supplying antisense constructs of certain oncogenes is also contemplated. Exemplary oncogenes that are appropriate targets for antisense constructs include ras, myc, neu, raf, erb, src, fms, jun, trk, ret, gsp, hst, bcl and abl.

Vectors expressing chemotherapeutic agents and toxins are further examples of anticellular agents capable of killing or suppressing the cell growth or division of tumor-associated endothelial cells. Exemplary chemotherapeutic agents include IFNs, TNF-α and IL-12. Exemplary cytotoxic agents include mammalian cell-, plant-, fungus- and bacterial-derived toxins, such as diphtheria toxin, Pseudomonas exotoxin, ricin A chain and deglycosylated ricin A chain. All such chemotherapeutic agents and toxic agents may be used in connection with the present invention.

The vectors may also be used to express an enzyme capable of converting a non-toxic pro-drug into a cytotoxic drug. Examples of this are the herpes simplex virus (HSV) thymidine kinase (tk) enzyme and the cytosine deaminase enzyme.

The vectors may be plasmids, retroviral vectors in recombinant retroviruses, adeno-associated virus (AAV) vectors in AAV virions, adenoviral vectors in replication-deficient adenovirus, and the like. Recombinant vectors may also be included within cells or liposomes.

In E-selectin-mediated gene therapy, the vascular endothelium is transfected using previously described techniques. For example, carotid arteries and internal jugular veins of New Zealand White rabbits were infected with recombinant adenovirus encoding either firefly luciferase or a nuclear-localizing variant of beta-galactosidase (Willard, 1994). Delivery of recombinant virus was achieved by one of four methods: (1) instillation within a surgically isolated vessel segment (dwell), (2) a double-balloon catheter, (3) a perforated balloon catheter (Wolinsky), or (4) an angioplasty balloon catheter coated with a hydrophilic adsorbent polymer (Hydrogel). Prototype catheters permit relatively efficient direct gene transfer to vascular endothelium.

Accumulation of vascular smooth muscle cells as a consequence of arterial injury is a major feature of vascular proliferative disorders. Molecular approaches to the inhibition of smooth muscle cell proliferation in these settings could potentially limit intimal expansion. This problem was approached by introducing adenoviral vectors encoding the herpes virus thymidine kinase (tk) into porcine arteries that had been injured by a balloon on a catheter (Ohno et al., 1994). These smooth muscle cells were shown to be infectable with adenoviral vectors, and introduction of the tk gene rendered them sensitive to the nucleoside analog ganciclovir. When this vector was introduced into porcine arteries immediately after a balloon injury, intimal hyperplasia decreased after a course of ganciclovir treatment. No major local or systemic toxicities were observed. These data suggest that transient expression of an enzyme that catalyzes the formation of a cytotoxic drug locally may limit smooth muscle cell proliferation in response to balloon injury.

EXAMPLE XV

Irradiation Following E-selectin-Mediated Cellular Delivery

As a specific guideline to even further exemplify the use of the present invention, the following protocol is provided. Tumors are irradiated with about 5 to 10 Gy followed by administration of HL525 clones containing the radiation-inducible Egr-TNF genetic construct at 4 hours after irradiation. HL525 clones then bind to E-selectin within the irradiated filed. A second radiation dose is given to the tumor about one hour after administration of HL525. This dose activates TNF induction, which is produced locally in the tumor vasculature.

Human T cells are infected with the murine retrovirus Moloney murine sarcomna virus containing the radiation-inducible Egr-TNF genetic construct. These infected T cells are given to patients after irradiation of the tumor site with about 5 to 10 Gy, as above. A second x-ray dose is again given to the tumor, about one hour later, to activate TNF induction in the local tumor vasculature.

EXAMPLE XVI

Pharmaceutical Compositions and Delivery

Aqueous compositions of the present invention comprise an effective amount of the E-selectin-targeting agent:selected agent conjugate dissolved or dispersed in a pharmaceuticaly acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes and lotions, and even mouthwashes, inhalents and the like.

To formulate the compounds or cells for parenteral administration, e.g., for injection via the intravenous, intramuscular or sub-cutaneous routes, typically, such compositions will be prepared as injectables, either as liquid solutions or suspensions; solid forms suitable for using to prepare solutions or suspensions upon the addition of a liquid prior to injection; or as emulsified preparations.

Solutions of the E-selectin-based active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Anti-E-selectin antibodies and saccharides and conjugates thereof can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The preparation of more, or highly, concentrated solutions for intramuscular injection is also contemplated where necessary. In this regard, the use of DMSO as solvent is contemplated as this will result in extremely rapid penetration, delivering high concentrations of the active agents to a small area. Therapeutic formulations in accordanvce with the present invention may also be reconstituted in the form of mouthwashes, in conjunction with antifungal reagents. Inhalant forms are also envisioned, which again, may contain the active agents alone, or in conjunction with other agents, such as, e.g., pentamidine.

The therapeutic formulations of the invention may also be prepared in forms suitable for topical administration, such as in cremes and lotions. These forms are envisioned to be particularly suitable for additionally treating radiation induced dermatitis. The preparation of oleaginous or water-soluble ointment bases is also well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates. Even delivery through the skin may be employed if desired, e.g., by using transdermal patches, iontophoresis or electrotransport.

The E-selectin-directed agents of the invention may also be advantageously employed for the preparation of ophthalmic solutions. Thus, for these embodiments, a conjugate or active composition of the invention would be administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparation will generally contain active agents in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The ophthalmic preparation will be administered topically to the eye of the subject in need of treatment by conventional methods, for example in the form of drops or by bathing the eye in the ophthalmic solution.

In certain embodiments, active compounds may be administered orally. This is contemplated for agents that are generally resistant, or have been rendered resistant, to proteolysis by digestive enzymes. Such compounds are contemplated to include chemically designed or modified agents; dextrorotatory peptidyl agents, e.g., as may used in combination with other E-selectin binding agents; and peptide and liposomal formulations in time release capsules to avoid peptidase and lipase degradation.

For oral adminstration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

EXAMPLE XVII

Determining the Level of Radiation Exposure

Anti-E-selectin can be used to visualize any vasculature following irradiation. This will be used for diagnostic radiology such as SPEC scanning.

Again, although the present invention provides a surprising use of E-selectin, in that it is to be specifically induced using radiation, other methods are available that can now be used in conjunction with the invention. In that the present methods for determining the level of radiation exposure are generally based upon determining the levels of E-selectin in exposed animals or patients, previously described methods for quantifying E-selectin are envisioned to be particularly useful.

For example, Keelan et al. (1994a) have studied endothelial luminal surface expression of E-selectin in vivo in the pig. Here, intravenous interleukin-1 (IL-1 infusion for 2 h) was used to induce E-selectin expression in various organs, as shown by immunostaining and selective clearance of intravenous 111In- or 99mTc-labeled anti-E-selectin MAb (1.2B6) compared with radiolabeled immunoglobulin G1 control.

Skin sites injected with IL-1, tumor necrosis factor, phytohemagglutinin, or phorbol myristate acetate at various times (45 min-24 h) before exsanguination showed specific accumulation of MAb 1.2B6 when 99mTc-MAb 1.2B6 and 111In-control immunoglobulin G1 were injected intravenously 10 min before exsanguination (Keelan et al., 1994a). This was maximal in 2-h after IL-1 and tumor necrosis factor lesions and after 9 h in phytohemagglutinin and phorbol myristate acetate lesions.

Keelan et al. (1994b) also assessed the imaging potential of an anti-E-selectin Mab 1.2B6 in a model of arthritis in the pig. Injection of phytohaemagglutinin (PHA) into a knee led to E-selectin expression on vessels in the synovium and draining deep inguinal lymph nodes, as demonstrated by immunohistology. No E-selectin expression was seen in the control knee injected with buffer alone. Animals were given 111In-Mab 1.2B6 or 111In-control antibody intravenously 3 hr after the intra-articular injection of PHA. Scintigraphy performed 24 hr after 111In-Mab 1.2B6 injection showed obvious localization of activity in the inflamed knee in each of three animals. Radiolabeled anti-E-selectin Mab was thus successfully used to image localized inflammatory tissues (Keelan et al., 1994b).

This approaches of Keelan et al. (1994a;b) to quantify changes in vascular luminal expression of E-selectin in models of inflammation and arthritis is considered as a suitable model for adaptation for analyzing E-selectin changes in relation to radiation treatment or damage.

Silber et al. (1994) showed that intravenous infusions of neutralizing doses of F(ab')2 fragments of murine antibodies to E-selectin during the early inductive phases of delayed hypersensitivity (DHR) resulted in IgG localization to dermal endothelium. The relative numbers of lymphocytes localized to the inflammatory site were significantly reduced in DHR modified with infusions of antibodies to E-selectin, while the numbers of lymphocytes recruited to skin in the animal given F(ab')2 fragments of an irrelevant murine monoclonal antibody of the same isotype and at the same dose were not changed (Silber et al. 1994).

Chapman et al. (1994) described the non-invasive imaging of E-selectin expression by activated endothelium in urate crystal-induced arthritis. In this study, they assessed the expression of E-selectin during the evolution of urate crystal-induced arthritis, using a radiolabeled MAb imaging technique. Monosodium urate (MSU) crystals and saline alone were injected respectively into the right (inflamed) and left (control) knees of 3 young pigs. Four hours later, 111In-labeled 1.2B6 F(ab')2 (anti-E-selectin MAb) and 125I-labeled MOPC 21 F(ab')2 (control MAb) were injected intravenously. Uptake of 1.2B6 in inflamed and control joints was assessed by scintigraphy 7 and 24 hours after intraarticular injection of MSU crystals. Immunohistochemistry studies and radioactivity counting of tissues were performed postmortem to confirm the observations from scintigraphy.

In the Chapman et al. (1994) studies, MAb 1.2B6 F(ab')2 scintigraphic images of the knees revealed a significantly increased uptake in the right (inflamed) knee at 7 and 24 hours postinjection, particularly over the joint space. These in vivo images were consistent with E-selectin expression in the inflamed tissue detected by immunohistochemistry. E-selectin is expressed by synovial endothelium during the evolution of urate crystal-induced arthritis and can be detected noninvasively using a radiolabeled MAb.

This E-selectin imaging technique of Chapman et al. (1994) is also envisioned as a useful noninvasive method for assessing E-selectin expression following radiation.

Gosset et al. (1995) also evaluated the expression of E-selectin on endothelium and epithelium in bronchial biopsies obtained from patients with allergic and non-allergic asthma. Bronchial biopsies were taken in asthmatic patients and control subjects (n=10) by fiberoptic bronchoscopy and embedded in paraffin. The cellular infiltrate was evaluated by May-Grunwald-Giemsa staining. Adhesion molecule expression was analyzed by immunohistochemistry using mouse monoclonal antibodies; the results were expressed as the percentage of positive cells.

The Gosset et al. (1995) method is another method that could be employed using the invention. Biopsies would be obtained from patients after radition and the E-selectin level determined to give an indication of radiation exposure.

EXAMPLE XVIII

Treating and Preventing Radiation Damage

This invention also provides compositions and methods for use in preventing or treating radiation-induced inflammation using E-selectin-based therapeutics in the absence of a second selected agent.

Human leukemia cell line HL60 has been used to quantify leukocyte adhesion to endothelial cells (Jones et al., 1995). HL60 cells were added to HUVECs after exposure to 10 Gy or cells treated with otherwise identical conditions without irradiation. Cultures were washed and cells were counted using a hemocytometer. Consecutive cell washes of culture revealed increased binding of HL60 cels at 4 h after irradiation as compared to untreated controls. Glycyrrhizin, carminic acid or sialyl Lewis X (1 mM each, SIGMA) were added to irradiated cells at 4 h after irradiation and 30 min prior to the addition of HL60 cells. Each agent blocked the adherence of HL60 cells to irradiated HUVECs.

Radiation is known to induce pneumonitis, cystitis, mucositis, esophagitis, dermatitis, neutrophilic vasculitis, acute pulmonary radiation injury and interstitial inflammation (Slauson et al., 1976; Dunn et al., 1986; Ward et al., 1993; Narayan, 1982; Fajardo and Berthrong, 1988; Hopewell et al., 1993), each of which can be treated using this invention. Animal models are also available for studying radiation-induced diseases, e.g., as described by Ward et. al.

(1993) for the study of radiation-induced pulmonary edema, alveolitis and fibrosis. Such models are intended for use in optimizing appropriate doses.

Following approval by the FDA, glycyrrhizin, carminic acid, sialyl Lewis X, a sialyl Lewis X/A mimic, or other signaling inhibitors, are to be used in phase I trials in patients undergoing radiotherapy. Glycyrrhizin is used as an antiinflammatory agent in Asia (Kanoka et al., 1990; Narasinga Rao et al., 1994), and so is safe for clinical use. These E-selectin-binding agents will be administered to patients receiving radiation therapy as topical pharmaceuticals in water based creams as treatment for radiation dermatitis. The advantage of these agents over glucocorticoid creams is that glucocorticoids slow would healing and re-epithelialization (Fajardo and Berthrong, 1988). After efficacy is demonstrated, these agents will be used as intravenous injections and oral preparations in phase I dose escalation trials to treat severe radiation inflammation, such as in the lung and pericardium.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbassi et al., "E-selectin supports neutrophil rolling in vitro under conditions of flow," *J Clin Invest*, 92(6): 2719–30, 1993.

Ades et al., "HMEC-1: establishment of an immortalized human microvascular endothelial cell line," *J. Invest. Dermatol.*, 99:683–690, 1992.

Alao et. al., *Journal of Pharmacy & Pharmacology*, 46(2): 135–7, 1994.

Allen and Choun, "Large unilamellar liposomes with low uptake into the reticuloendothelial system," *FEBS Lett.*, 223:42–46, 1987.

Alon et. al., *J. Cell Biol.*, 127(5):1485–95, 1994.

Barker et al., "Clinical experience of inflammatory breast carcinoma of the breast with or without chemotherapy," *Cancer*, 45:625–9, 1980.

Behrends et al., "ICAM," *J. Invest. Dermat.*, 1994.

Berg et al., "A carbohydrate domain common to both sialyl Le(a) and sialyl Le(X) is recognized by the endothelial cell leukocyte adhesion molecule ELAM-1," *J Biol Chem*, 266(23):14869–72, 1991.

Betageri et al., *Journal of Pharmacy & Pharmacology*, 45(1):48–53, 1993.

Bevilacqua, "Endothelial-leukocyte adhesion molecules," *Annu. Rev. Immunol.*, 11:767–804, 1993.

Bevilacqua et al., "Endothelial leukocyte adhesion molecule 1: an inducible receptor for neutrophils related to complement regulatory proteins and lectins," *Science*, 243:1160–1165, 1989.

Bicknell, "Vascular targeting and the inhibition of angiogenesis *Annals of Oncology*, 4:45–50, 1994.

Bochner et. al., *J. Immunol.*, 152(2):774–82, 1994.

Bode et al., *Science*, 229(4715):765–7, 1985.

Brach et al., "Ionizing radiation stimulates NF-kB binding activity in human myeloid leukemia cells," *J. Clin. Invest.*, 88:691–695, 1991.

Braslawsky et al., *Cancer Research*, 50(20):6608–14, 1990.

Brunner et al., "Xenograft model of progressive human proliferative breast disease," *J. Natl. Cancer Institute*, 85(21):1725–32, 1993.

Byers et al., *Cancer Res.*, 49:6153–6160, 1989.

Campbell, in Monoclonal Antibody Technology, Laboratory Techniques in Biochemistry and Molecular Biology Vol. 13, Burden and Von Knippenberg, Eds. pp. 75–83, Amsterdam, Elseview, 1984

Caplen et al., "Liposome-mediated CFTR gene transfer to the nasal epithelium of patients with cystic fibrosis," *Nature Medicine*, 1(1):39–46, 1995.

Casey et. al., Growth suppression of human breast cancer cells by the introduction of a wild-type p53 gene. Oncogene 6: 1791–1797, 1991.

Cavenagh et al., "Acute myeloid leukaemia blast cells bind to human endothelium in vitro utilizing E-selectin and vascular cell adhesion molecule-1 (VCAM-1)," *Br J Haematol*, 85(2):285–91, 1993.

Chapman et al., "Noninvasive imaging of E-selectin expression by activated endothelium in urate crystal-induced arthritis," *Arthritis Rheum*, 37(12):1752–6, 1994.

Chomczynski and Sacchi, "Single-step method of RNA isolation by acid guanidinium thiocyanate-phenol-chloroform extraction," *Analytical Biochemistry*, 162:156–159, 1987.

Cliff, "The acute inflammatory reaction in the rabbit ear chamber," *J. Exp. Med.*, 124:546–556, 1966.

Collen et al., *Circulation*, 82(5):1744–53, 1990.

Collins, "Endothelial nuclear factor-kappa B and the initiation of the atherosclerotic lesion," *Laboratory Investigation.*, 68:499–508, 1993.

Collins et al., "Structure and chromosomal location of the gene for endothelial-leukocyte adhesion molecule 1," *J. Biol. Chem.*, 266:2466–2473, 1991.

Couvreur, "Polyalkyleyanoacrylates as colloidal drug carriers," Crit. *Rev. Ther. Drug Carrier Syst.*, 5:1–20, 1988.

Davis and Morris, *Mol. Cell Endocrinol.*, 1:5–6, 1991.

De Boer et. al., *Immunology*, 81(3):359–65, 1994.

DeSombre et al., "Comparison of the distribution of bromine-77-bromovinyl steroidal and triphenylethylene estrogens in the immature rat," *Journal of Nuclear Medicine*, 31(9):1534–42, 1990.

Deshpande et al., "Copper-67-labeled monoclonal antibody Lym-1, a potential radiopharmaceutical for cancer therapy: labeling and biodistribution in RAJI tumored mice." *Journal of Nuclear Medicine*, 29(2):217–25, 1988.

Dowell et al., "Effects of a xanthine oxidase/hypoxanthine free radical and reactive oxygen species generating system on endothelial function in New Zealand white rabbit aortic rings.," *Journal of Cardiovascular Pharmacology.*, 22:792–797, 1993.

Dunn et al., "Effects of irradiation on endothelial cell-PMN leukocyte interaction," *J. Appl. Physiol.*, 60:1932–1937, 1986.

Eldor et al., "Arachidonic metabolism and radiation toxicity in cultures of vascular endothelial cells," *Prostaglandis leukotrienes and essential fatty acids*, 36:251–258, 1989.

Eldor et al., "Perturbation of endothelial functions by ionizing irradiation: effects on prostaglandins, chemoattractants and mitogens," *Semin Thromb Hemost*, 15:215–225, 1989.

Epenetos et al., *Cancer Res.*, 46:3183–3191, 1986.

Etingin et al., "Identification of a monocyte receptor on herpesvirus-infected endothelial cells," *Proc. Natl. Acad. Sci. USA*, 88:7200–7203, 1991.

Fajardo and Berthrong, "Vascular lesions following radiation," *Pathol. Annu.*, 23:297–330, 1988.

Fastenberg, *Am. J. Clin. Oncol.*, 8:134, 1985.

Finco and Baldwin, "Kappa B site-dependent induction of gene expression by diverse inducers of nuclear factor kappa B requires Raf-1," *Journal of Biological Chemistry*, 268:17676–17679, 1993.

Fletcher and Shukovsky, "The interplay of radiocurability and tolerance in the irradiation of human cancers," *J. Radiol. Electrol.*, 56:383–400, 1975.

Fraker and Speck, "Protein and cell membrane iodination," *Biochem. Biophys. Res. Com.*, 80:849, 1989.

Gabizon and Papahadjopoulos, "Liposomes formulations with prolonged circulation time in blood and enhanced uptake by tumors," *Proc. Natl. Acad. Sci. USA*, 85:6949–6953, 1988.

Gefter et al., *Somatic Cell Genet.* 3:231–236 (1977)

Ghersa et al., "Labile proteins play a dual role in the control of endothelial leukocyte adhesion molecule-1 (ELAM-1) gene regulation," *J. Biol. Chem.*, 267(27):19226–32, 1992.

Glaser, "Cell Adhesion-Molecular Based Drugs Test the Waters in the Clinical Area," *Genetic Engineering News*, 1994.

Goding, 1986, in Monoclonal Antibodies: Principles and Practice, 2d ed., Orlando, Fla., Academic Press, 1986, pp. 60–61, 65–66, 71–74.

Goelz, S. E., Hession, C., Goff, D., et. al., *Cell* 63, 1349–1356, 1990.

Goelz et al., "Differential expression of an E-selectin ligand (SLex) by two Chinese hamster ovary cell lines transfected with the same alpha (1,3)-fucosyltransferase gene (ELFT)," *J Biol Chem*, 269(2):1033–40, 1994.

Gosset et al., "Expression of E-selectin, ICAM-1 and VCAM-1 on bronchial biopsies from allergic and non-allergic asthmatic patients," *Int Arch Allergy Immunol*, 106(1):69–77, 1995.

Green et al., "High Affinity Binding of the Leucocyte Adhesion Molecule L-Selectin to 3'-Sulphated-Le and -Le$^x$ Oligosaccharides and the Predominance of Sulphate in this Interaction Demonstrated by Binding Studies with a Series of Lipid-Linked Oligosaccharides," *Biochemical and Biophysical Research Communications*, 188(1) : 244–251, 1992.

Grinnell et. al., *Glycobiology*, 4(2):221–5, 1994.

Groves et al., "Endothelial leucocyte adhesion molecule-1 (ELAM-1) expression in cutaneous inflammation," *Br J Dermatol*, 124(2):117–23, 1991.

Gustafson et al., "Hydrogen peroxide stimulates phospholipase A2-mediated arachidonic acid release in cultured intestinal epithelial cells (INT 407)," *Scand. J. Gastroenterol*, 26:237–247, 1991.

Gutierrez et al., "Gene therapy for cancer," *Lancet*, 339 (8795):715–21, 1992.

Haagensen, "Diseases of the Breast," 2 ed., Phil., Pa.: WB Saunders, p.623, 1971.

Hakkert et al., "Neutrophil and monocyte adherence to and migration across monolayers of cytokine-activated endothelial cells: the contribution of CD18, ELAM-1, and VLA-4," *Blood*, 78(10):2721–6, 1991.

Hallahan et al., "Increased tumor necrosis factor alpha mRNA after cellular exposure to ionizing radiation," *Proc. Natl. Acad. Sci. USA*, 86:10104–10107, 1989.

Hallahan et al., "Tumor necrosis factor gene expression is mediated by protein kinase C following activation by ionizing radiation," *Cancer Research*, 51:4565–4569, 1991.

Hallahan et al., "Radiation signalling mediated by Jun activation following dissociation from the Jun inhibitor," *J. Biol. Chem.*, 268:4903–7, 1992.

Hallahan et al., "Membrane-derived second messengers mediate radiation induced TNF gene induction," *Proc. Natl. Acad. Sci.*, 91:4897–4901, 1993.

Hallahan et al., "The Role of Cytokines in Radiation Oncology. Important advances in Oncology," ed. H. DeVita, Rosenberg, Philadelphia, Pa.: Lippincott, 1993.

Harris et al., "Gene therapy through signal transduction pathways and angiogenic growth factors as therapeutic targets in breast cancer," *Cancer*, 74:1021–5, 1994.

Hasegawa et. al., *Carbohydrate Research*, 257(1):67–80, 1994.

Henry-Michelland et al., "Attachment of antibiotics to nanoparticles; Preparation, drug-release and antimicrobial activity in vitro, *Int. J. Pharm.*, 35:121–127, 1987.

Hollstein, M., Sidransky, D., Vogelstein, B., and Harris, C., p53 mutations in human cancers. *Science*, 253: 49–53, 1991.

Hopewell et al., "Microvasculature and radiation damage. Acute and Long-term side effects of radiotherapy," ed. W. Hinkelbein et al., Berlin: Springer-Verlag, 1993.

Hwu et al., "Functional and molecular characterization of tumor-infiltrating lymphocytes transduced with tumor necrosis factor-alpha cDNA for the gene therapy of cancer in humans," *Journal of Immunology*, 1993.

Jaenke et al., "Capillary endothelium. Target site of renal radiation injury," *Lab Invest*, 68:396–405, 1993.

Jones et al., "A two step adhesion cascade for T cell/ endothelial cell interactions under flow conditions," *J. Clin. Invest.*, 94:2443–2450, 1995.

Jones and Shenk, "Isolation of Adenovirus Type 5 Host Range Deletion Mutants Defective for Transformation of Rat Embryo Cells," *Cell*, 17:683–689, 1979.

Jutila et al., "Characterization of a functionally important and evolutionarily well-conserved epitope mapped to the short consensus repeats of E-selectin and L-selectin," *J Exp Med*, 175(6):1565–73, 1992.

Kamb et. al., *Science*, 264:436–440, 1994.

Kameyama et al. (1991).

Kancka et al., "Preparation of bovine serum albumin conjugate and glycyrrhetic acid," *Chemical and Pharmaceutical bulletin*, 38:221–4, 1990.

Keelan et al., "Characterization of E-selectin expression in vivo with use of a radiolabeled monoclonal antibody,"*Am J Physiol*, 266(1 Pt 2) pH278–90, January 1994a.

Keelan et al., "Imaging vascular endothelial activation: an approach using radiolabeled monoclonal antibodies against the endothelial cell adhesion molecule E-selectin," *J Nucl Med*, 35(2):276–81, February 1994b.

Kharbanda et al., "Activation of the src-like tyrosine kinase by ionizing radiation," *J. Biol. Chem.*, 269:20739–20743, 1994.

Kishimoto et al., "Antibodies against human neutrophil LECAM-1 (LAM-1/Leu-8/DREG-56 antigen) and endothelial cell ELAM-1 inhibit a common CD18-independent adhesion pathway in vitro," *Blood*, 78(3):805–11, 1991.

Klein, "Yt-90 an I-131 radioimmunoglobin therapy of experimental hepatoma," *Cancer Res.*, 49:6383, 1989.

Klibanov et al., *American Journal of Physiology*, 261(4 Suppl):60–5, 1991.

Kohler and Milstein, *Nature*, 256:495–497 (1975)

Kohler and Milstein, *Eur. J. Immunol.*, 6:511–519 (1976)

Kojima et al., "Multi-recognition capability of E-selectin in a dynamic flow system, as evidenced by differential effects of sialidases and anti-carbohydrate antibodies on selectin-mediated cell adhesion at low vs. high wall shear stress: a preliminary note," *Biochem Biophys Res Commun*, 189(3):1686–94, 1992.

Konno et al., "Antitumor effect of adriamycin entrapped in liposomes conjugated with anti-human alpha-fetoprotein monoclonal antibody, *Cancer Research*, 47(16):4471–7, 1987.

Koong et al., "Hypoxia causes the activation of nuclear factor kappa B through the phosphorylation of I kappa B alpha on tyrosine residues," *Cancer Research*, 54:1425–1430, 1994.

Krahenbuhl et. al.,*J. Clin. Endocrinol. Metab.*, 78(3):581–5, 1994.

Kumar et al., *J. Biol. Chem.* 266, 21777–21783, 1991.

Kunich et al., *Molec. Cell. Biol.*, 12:4412, 1992.

Larsson and Cerutti, "Translocation and enhancement of phosphotransferase activity of protein kinase C following exposure in mouse epidermal cells to oxidants," *Cancer Research*, 49:5627–5632, 1989.

Le Doussal et. al., *Int. J. Cancer Suppl.*, 7:58–62, 1992.

Leichner et. al., "An overview of imaging techniques and physical aspects of treatment planning in radioimmunotherapy", *Med. Phys.*, 20(2 Pt 2):569–77, 1993.

Lenter et. al., *J. Cell Biol.*, 125(2):471–81, 1994.

Lessem et al., "Accumulation of technetium-99m pyrophosphate in experimental infarctions in the rat," *Cardiovascular Research*, 14(6):352–9, 1980.

Li and Sedivy, "Raf-1 protein kinase activates the NF-kappa B transcription factor by dissociating the cytoplasmic NF-kappa B-I kappa B complex," *Proceedings of the National Academy of Sciences of the United States of America*, 90:9247–9251, 1993.

Lo et al., "E-selectin ligands mediate tumor necrosis factor-induced neutrophil sequestration and pulmonary edema in guinea pig lungs," *Circ Res*, 75(6):955–60, 1994.

Lowe et al., *Cell*. 63, 475–484, 1990.

Lowe et al., *J. Biol. Chem.* 266, 21777–21783, 1991.

Luders et al., *Cancer Immunology, Immunotherapy*, 20(1):85–90, 1985.

Malik, "The activity of TNF in experimental animal models. In: Beutler, B (Ed) Tumor necrosis factor," New York, N.Y., 1992.

Marx, *Science*, 263:319–321, 1994.

Matthay et al., *Cancer Research*, 49(17):4879–86, 1989.

Matzner et al., "Generation of lipid neutraphil chemoattractants by irradiated BAEC," *J. Immunol.*, 140:2681–2685, 1988.

McGrory et al., *Virology*, 163:614–7, 1988.

Mehta et al. *International Journal of Radiation Oncology, Biology, Physics.* 19(3):627–31, 1990.

Meyer et al., "H2O2 and antioxidants have opposite effects on activation of NF-kappa B and AP-1 in intact cells: AP-1 as secondary antioxidant-responsive factor," *Embo. J.*, 12:2005–2015, 1993.

Miller et al., "Selection of a highly tumorigenic breast cancer cell line sensitive to estradiol to evidence in vivo the tumor-inhibitory effect of butyrate derivative Monobut-3," *Life Sciences*, 55(12):951–9, 1994.

Montefort et al., "Intercellular adhesion molecule-1 (ICAM-1) and endothelial leucocyte adhesion molecule-1 (ELAM-1) expression in the bronchial mucosa of normal and asthmatic subjects," *Eur Respir J*, 5(7):815–23, 1992.

Montgomery et al., "Activation of endothelial-leukocyte adhesion molecule 1 (ELAM-1) gene transcription," *Proc. Natl. Acad. Sci. USA*, 88:6523–6527, 1991.

Moughal et al., "Endothelial cell leukocyte adhesion molecule-1 (ELAM-1) and intercellular adhesion molecule-1 (ICAM-1) expression in gingival tissue during health and experimentally-induced gingivitis," *J Periodontal Res*, 27(6):623–30, 1992.

Mulligan et al., "Role of Endothelial Leukocyte Adhesion Molecule 1 (ELAM01) in Neutrophil-mediated Lung Injury in Rats," *J. Clin. Invest.*, 88:1396–1406, 1991

Mulligan et al., "Protective Effects of Sialylated Oligosaccharides in Immune Complex-induced Acute Lung Injury," *J. Exp. Med.*, 178:623–631, 1993.

Munro et al., "Expression of sialyl-Lewis X, an E-selectin ligand, in inflammation, immune processes, and lymphoid tissues," *Am J Pathol*, 141(6):1397–408, 1992

Nabel, "Gene transfer and vascular disease" *Cardiovascular Research*, 28(4):445–55, 1994.

Narasinga Rao et al., "Sialyl Lewis X mimics derived from a Pharmacophore search are selectin inhibitors with anti-inflammatory activity," *J. Biol. Chem.*, 269:19663–19666; 1994.

Narayan and Cliff, "Morphology of irradiated microvasculature," *Am. J. Pathol.*, 106:47, 1982.

Nelson et al., "Higher-affinity oligosaccharide ligands for E-selectin," *J. Clin. Invest.*, 91:1157–1166, 1993.

Neumann et al., "Immunohistochemistry of port-wine stains and normal skin with endothelium-specific antibodies PAL-E, anti-ICAM-1, anti-ELAM-1, and anti-factor VIIIrAg,", *Arch Dermatol*, 130(7):879–83, 1994.

Norton et al., "Characterization of murine E-selectin expression in vitro using novel anti-mouse E-selectin monoclonal antibodies," *Biochem Biophys Res Commun*, 195 (1):250–8, 1993.

Numazaki et. al., *Tohoku Journal of Experimental Medicine*, 172(2):147–53, 1994.

Ohno et al., "Gene therapy for vascular smooth muscle cell proliferation after arterial injury," *Science*, 265(5173):781–4, 1994.

Olofsson et al., "E-selectin mediates leukocyte rolling in interleukin-1-treated rabbit mesentery venules," *Blood*, 84(8):2749–58, 1994.

Okuno et. al., *Nippon Rinsho—Japanese Journal of Clinical Medicine*, 52(7):1823–1827, 1994.

Pai et al., "Antitumor effects of B3-PE and B3-LysPE40 in a nude mouse model of human breast cancer and the evaluation of B3-PE toxicity in monkeys," *Cancer Research*, 52(11):3189–93, 1992.

Patel et al., "Oxygen radicals induce human endothelial cells to express GMP-140 and bind neutrophils," *J. Cell Biol.*, 112:749–759, 1991.

Phillips et. al., "ELAM-1 Mediates Cell Adhesion by Recognition of a Carboydrate Ligan, Sialyl-Le$^x$," *Science*, 250:1130–1132, 1990.

Pinola et. al., *J. Immunol.*, 152(2) :774–82, 1994.

Pober and Cotran, "Cytokines and endothelial cell biology," *Physiol. Rev.*, 70:427, 1990.

Porras et al., "Dissociation," *J. Biol. Chem.*, 269:12741, 1994.

Prasad et al., "Activation of Nuclear Factor κB in Human Lymphoblastoid Cells by Low-Dose Ionizing Radiation," *Radiation Research*, 138:367–372, 1994.

Read et al., "NFkB. An inducible regulatory system in Endothelial Cells," *J. Exp. Med.*, 179:503, 1994.1994.

Reinhold et al., "The vascular system," *Adv. Rad. Biol.*, 14:177–226, 1990.

Roeske et. al., "Modeling of dose to tumor and normal tissue from intraperitoneal radioimmunotherapy with alpha and beta emitters.", *Int. J. Radiation Oncology Biol. Phys.*, 19:1539–48, 1990.

Saluson et al., "Inflammatory sequences in acute pulmonary radiation injury," 82:529–572, 1976.

Sands, *Immunoconjugates and Radiopharmaceuticals*, 1:213–226, 1988.

Schreck et al., "Nuclear factor kappa B: an oxidative stress-responsive transcription factor of eukaryotic cells" *Free Radic. Res. Commun.*, 17:221–237, 1992.

Schreck et al., "Reactive oxygen intermediates as apparently widely used messengers in the activation of the NF-κB transcription factor and HIV-1," *The EMBO Journal*, 10(8):2247–2258, 1991.

Schreiber et al., *Nucleic Acids Res.*, 17:6419, 1989.

Scott et al., *Journal of the National Cancer Institute*, 79(5): 1163–72, 1987

Sedmak et al., "Divergent patterns of ELAM-1, ICAM-1, and VCAM-1 expression on cytomegalovirus-infected endothelial cells," *Transplantation*, 58(12):1379–85, 1994.

Silber et al., "Recruitment of lymphocytes during cutaneous delayed hypersensitivity in nonhuman primates is dependent on E-selectin and vascular cell adhesion molecule 1," *J Clin Invest*, 93(4):1554–63, 1994.

Slauson et al., "Inflammatory sequences in acute pulmonary radiation injury," *Am. J. Path.*, 82:549–572, 1976.

Soma et. al., *Endocrine Regulations*, 28(1):31–34, 1994.

Span et al., "Cytomegalovirus induced PMN adherence in relation to an ELAM-1 antigen present on infected endothelial cell monolayers," *Immunology*, 72(3):355–60, 1991.

Sporn et al., "E-selectin-dependent neutrophil adhesion to Rickettsia rickettsii-infected endothelial cells," *Blood*, 81(9):2406–12, 1993.

Springer, "Traffic signals for lymphocyte recirculation and leukocyte emigration: the multistep paradigm," *Cell*, 76:301–314, 1994.

Steinberg et al., "Survival in lung reperfusion injury is improved by an antibody that binds and inhibits L- and E-selectin," *J Heart Lung Transplant*, 13(2):306–18, Mar.–Apr. 1994.

Swerlick and Lawley, "Role of Microvascular Endothelial Cells in Inflammation," *HDMEC In Inflammation*, 100(1): 111S–1115s, 1993.

Terada et. al., *Carbohydrate Research*, 259(2):210–18, 1994.

Treisman et al., "Upregulation of tumor necrosis factor-alpha production by retrovirally transduced human tumor-infiltrating lymphocytes using trans-retinoic acid," *Cellular Immunology*, 156(2):448–57, 1994 July.

Trubetskoy et al., *Biochimica et Biophysica Acta*, 1131(3): 311–3, 1992.

Tsai et. al., *J. Pharmaceutical Sci.*, 81(9):961–3, 1992.

Tyrrell et al., "Structural requirements for the carbohydrate ligand of E-selectin," *Proc. Natl. Acad. Sci. USA*, 88:10372–10376, 1991.

Uckun et al., "Ionizing radiation stimulates tyrosine-specific protein kinases triggering apoptosis," *Proc. Natl. Acad. Sci.*, 89:9005–9009, 1992.

Ulich et al., "Intratracheal administration of endotoxin and cytokines: VIII. LPS induces E-selectin expression; anti-E-selectin and soluble E-selectin inhibit acute inflammation," *Inflammation*, 18(4):389–98, 1994.

Veale et al., "Reduced synovial membrane macrophage numbers, ELAM-1 expression, and lining layer hyperplasia in psoriatic arthritis as compared with rheumatoid arthritis," *Arthritis Rheum*, 36(7):893–900, 1993.

von Asmuth et al., "Evidence for endocytosis of E-selectin in human endothelial cells," *Eur J Immunol*, 22(10): 2519–26, 1992.

Wakita et al., "E-selectin and vascular cell adhesion molecule-1 as critical adhesion molecules for infiltration of T lymphocytes and eosinophils in atopic dermatitis," *J Cutan Pathol*, 21(1):33–9, 1994.

Walker, "Inducible DNA repair systems," *Ann. Rev. Biochem.*, 54:425–457, 1985.

Walz et. al., "Recognition by ELAM-1 of the Sialyl-Le$^x$ Determinant on Myeloid and Tumor Cells," *Science*, 250:1132–1135, 1990

Ward, "DNA damage produced by ionizing radiation in cells: mechanisms of formation and repairability," *Prog. Nucleic Acid Res*, 3:95, 1988.

Ward et al., "The pulmonary response to sublethal thoracic irradiation in the rat," *Radiat Res*, 136:15–21, 1993.

Weichselbaum et al., "Radiation targeting of gene therapy preferentially radiosensitizes tumor cells," *Cancer Research*, 54:4266–4269, 1994.

Weinberg, R. A., Tumor suppressor gene. *Science*, 254: 1138–1145, 1991.

Weiner et al., *Cancer Res.*, 49:4062–4067, 1989.

Whelan et al., "An NF kappa B-like factor is essential but not sufficient for cytokine induction of endothelial leukocyte adhesion molecule 1 (ELAM-1) gene transcription," *Nucleic Acids Res.*, 19:2645–2653, 1991.

Willard, "Genetic modification of the vessel wall. Comparison of surgical and x catheter-based techniques for delivery of recombinant adenovirus," *Circulation*, 89(5): 2190–7, 1994.

Williams and Roberts, "Signal transduction pathways involving the Raf proto-oncogene. *Cancer and Metastasis Reviews*, 13:105–116, 1994.

Williams et al., "Targeting of human glioma xenografts utilizing radiolabeled antibodies," *Int. J. Rad. Onc. Biol. Phys.*, 18:1367–1375, 1990.

Yoshida et. al., *Glycoconjugate Journal*, 10(1):3–15, 1993.

Yuen et al., "Novel Sulfated Ligands for the Cell Adhesion Molecule E-Selectin Revealed by the Neoglycolipid Technology among O-Linked Oligosaccharides on an Ovarian Cystadenoma Glycoprotein," *Biochemistry*, 31:9126–9131, 1992.

Yuen et al., "A Superior Oligosaccharide Ligand for Human E-Selectin," *The Journal of Biological Chemistry*, 269(3): 1595–1598, 1994.

Zhang et al., "A secreted mucin carrying sialyl-Lewis a from colon carcinoma cells binds to E-selectin and inhibits HL-60 cell adhesion," *Int J Cancer*, 59(6):823–9, 1994.

Ziegler et al., "Pyrrolidine dithiocarbamate inhibits NF-kappa B mobilization and TNF production in human monocytes," *J. Immunol.*, 151:6986–6993, 1993.

What is claimed is:

1. A method for delivering a selected agent to vascular endothelial cells of an animal, comprising inducing E-selectin or L-selectin expression in said vascular endothelial cells in said animal with ionizing radiation and administering to said animal a composition comprising an E-selectin or L-selectin targeting component and a selected agent, whereby the agent is delivered to vascular endothelial cells by said targeting component.

2. The method of claim 1, comprising inducing E-selectin expression in vascular endothelial cells.

3. The method of claim 1, comprising inducing L-selectin expression in vascular endothelial cells.

4. The method of claim 1, wherein E-selectin or L-selectin expression in vascular endothelial cells is induced by γ-irradiation.

5. The method of claim 1, wherein E-selectin or L-selectin expression in vascular endothelial cells is induced by x-rays.

6. The method of claim 1, wherein said vascular endothelial cells are diseased.

7. The method of claim 6, further defined as a method for delivering a selected agent to the disease-associated vasculature of an animal with diabetic retinopathy, vascular restenosis, arteriovenous malformation (AVM) or meningioma.

8. The method of claim 1, wherein said vascular endothelial cells are part of the vasculature of a tumor.

9. The method of claim 8, wherein E-selectin or L-selectin expression in vascular endothelial cells is induced by specific x-ray irradiation of the tumor site.

10. The method of claim 8, wherein said composition is administered to said animal parenterally.

11. The method of claim 8, wherein said composition is administered to said animal by injection into the tumor.

12. A method of delivering a protein to the vascular endothelial tissue of an animal comprising inducing E-selectin or L-selectin in cells of said vascular endothelial tissue with ionizing radiation and administering a T lymphocyte containing a recombinant vector that expresses said protein, whereby said protein agent is delivered to vascular endothelial tissues.

13. The method of claim 1, wherein said selected agent comprises a recombinant vector comprising a promoter operatively linked to a gene encoding a protein, wherein the vector expresses said protein in vascular a endothelial cell.

14. The method of claim 13, wherein said promoter is a radiation-inducible promoter.

15. The method of claim 14, wherein said promoter is a CArG domain of an Egr-1 promoter, a fos promoter, a c-jun promoter or TNF-α promoter operatively linked to a protein expression region.

16. The method of claim 13, wherein said promoter is a vascular endothelial cell specific promoter.

17. The method of claim 16, wherein said promoter is an Egr-1 promoter, and ICAM-1 promoter or an E-selecting gene promoter.

18. The method of claim 13, wherein said protein is a tumor suppressor protein, a chemotherapeutic agent, a cytotoxin or an agent that suppresses neovascularization.

19. The method of claim 18, wherein said protein is p53, p16, the retinoblastoma gene product or the Wilms' tumor gene product (WT1).

20. The method of claim 18, wherein said protein is IFN-α, IFN-βγ, IL-12 or TNF-α.

21. The method of claim 18, wherein said protein is an enzyme that converts a non-toxic pro-drug into a cytotoxic drug.

22. The method of claim 21, wherein said protein is a herpes simplex virus (HSV) thymidine kinase (tk) or cytosine deaminase.

23. The method claim 18, wherein said protein is a plant-, fungus- or bacteria-derived toxin.

24. The method of claim 23, wherein said protein is diphtheria toxin, Pseudomonas toxin, ricin A chain, or deglycosylated ricin A chain.

25. The method of claim 13, wherein said recombinant vector is a plasmid, a retroviral vector, an AAV vector, an HSV-1 vector, an HPV vector or an adenoviral vector.

* * * * *